(12) United States Patent
Mikoshiba et al.

(10) Patent No.: US 9,803,206 B2
(45) Date of Patent: Oct. 31, 2017

(54) **THERAPEUTIC AGENT FOR TREATING *TRYPANOSOMA*-ASSOCIATED DISEASE, METHOD FOR KILLING *TRYPANOSOMA* PARASITES, AND USE THEREOF**

(71) Applicant: RIKEN, Saitama (JP)

(72) Inventors: Katsuhiko Mikoshiba, Saitama (JP); Takeshi Nara, Tokyo (JP); Muneaki Hashimoto, Tokyo (JP)

(73) Assignee: RIKEN, Wako-Shi Saitama (JP)

( * ) Notice: Subject to any disclaimer, the term of this patent is extended or adjusted under 35 U.S.C. 154(b) by 0 days.

(21) Appl. No.: 14/509,262

(22) Filed: Oct. 8, 2014

(65) Prior Publication Data

US 2015/0099795 A1    Apr. 9, 2015

(30) Foreign Application Priority Data

Oct. 8, 2013  (JP) ................ 2013-211448

(51) Int. Cl.
*C07H 21/04*  (2006.01)
*C12N 15/113*  (2010.01)

(52) U.S. Cl.
CPC ...... *C12N 15/1138* (2013.01); *C12N 2310/11* (2013.01); *C12N 2310/315* (2013.01)

(58) Field of Classification Search
CPC .................................................. C07H 21/04
See application file for complete search history.

(56) References Cited

U.S. PATENT DOCUMENTS

2013/0296230 A1    11/2013 Mikoshiba et al.

FOREIGN PATENT DOCUMENTS

| JP | 08-508645 | 9/1996 |
|---|---|---|
| JP | 10-513343 | 12/1998 |
| JP | 2012-080804 | 4/2012 |
| WO | 94/23050 | 10/1994 |
| WO | 96/19580 | 6/1996 |
| WO | 2012/057294 | 5/2012 |

OTHER PUBLICATIONS

Militello et al. Molecular & Biochemical Parasitology 157 (2008) 17-126.*

Malaga, S. and Yoshida, N., "Targeted Reduction in Expression of Trypanosoma cruzi Surface Glycoprotein gp90 Increases Parasite Infectivity," Infection and Immunity, Jan. 2001, pp. 353-359.

Nakajima-Shimada, Junko, et al., "Inhibition of Trypanosoma cruzi Growth in Mammalian Cells by Purine and Pyrimidine Analogs," Antimicrobial Agents and Chemotherapy, Nov. 1996, pp. 2455-2458.

Huang, G., et al., "Acidocalcisomes of Trypanosoma brucei have an inositol 1,4,5-trisphosphate receptor that is required for growth and infectivity," PNAS, Jan. 29, 2013, vol. 110, No. 5, pp. 1887-1892.

Darocha, W.D., et al., "Tests of cytoplasmic RNA interference (RNAi) and construction of a tetracycline-inducible T7 promoter system in Trypanosoma cruzi," Molecular & Biochemical Parasitology, 133, 2004, pp. 175-186.

Barker, R.H., Jr., et al., "Inhibition of Plasmodium falciparum malaria using antisense oligodeoxynucleotides," Proc. Natl. Acad. Sci, USA, vol. 93, pp. 514-518, Jan. 1996.

Office Action for Japanese patent application No. 2013-211448, dated Jun. 20, 2017.

* cited by examiner

*Primary Examiner* — Kimberly Chong
(74) *Attorney, Agent, or Firm* — Casimir Jones, S.C.

(57) ABSTRACT

A therapeutic agent for treating a *Trypanosoma*-associated disease; a method of preventing infection by *Trypanosoma* parasites, or killing *Trypanosoma* parasites; and use thereof, the therapeutic agent and the method each using a mechanism different from a mechanism used in conventional technology. The therapeutic agent of the present invention for treating a *Trypanosoma*-associated disease includes, as a medicinal component, an antisense oligonucleotide suppressing the expression of an inositol 1,4,5-trisphosphate receptor protein of *Trypanosoma* parasites.

4 Claims, 2 Drawing Sheets

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Antisense nucleotide

<400> SEQUENCE: 1
ttccaagcct ccaccatccc                                          20

```
<210> SEQ ID NO 2
<211> LENGTH: 20
<212> TYPE: DNA
<213> ORGANISM: Artificial Sequence
<220> FEATURE:
<223> OTHER INFORMATION: Antisense nucleotide

<400> SEQUENCE: 2
tctcttccca gccaccacct                                            20

<210> SEQ ID NO 3
<211> LENGTH: 20
<212> TYPE: DNA
<213> ORGANISM: Artificial Sequence
<220> FEATURE:
<223> OTHER INFORMATION: Antisense nucleotide

<400> SEQUENCE: 3
gtcctccctt tccgtgctgt                                            20

<210> SEQ ID NO 4
<211> LENGTH: 20
<212> TYPE: DNA
<213> ORGANISM: Artificial Sequence
<220> FEATURE:
<223> OTHER INFORMATION: Antisense nucleotide

<400> SEQUENCE: 4
tcctcctccc ttccgccatt                                            20

<210> SEQ ID NO 5
<211> LENGTH: 20
<212> TYPE: DNA
<213> ORGANISM: Artificial Sequence
<220> FEATURE:
<223> OTHER INFORMATION: Sense nucleotide

<400> SEQUENCE: 5
gggatggtgg aggcttggaa                                            20

<210> SEQ ID NO 6
<211> LENGTH: 20
<212> TYPE: DNA
<213> ORGANISM: Artificial Sequence
<220> FEATURE:
<223> OTHER INFORMATION: Sense nucleotide

<400> SEQUENCE: 6
aggtggtggc tgggaagaga                                            20

<210> SEQ ID NO 7
<211> LENGTH: 20
<212> TYPE: DNA
<213> ORGANISM: Artificial Sequence
<220> FEATURE:
<223> OTHER INFORMATION: Sense nucleotide

<400> SEQUENCE: 7
acagcacgga aagggaggac                                            20

<210> SEQ ID NO 8
<211> LENGTH: 20
<212> TYPE: DNA
<213> ORGANISM: Artificial Sequence
<220> FEATURE:
<223> OTHER INFORMATION: Sense nucleotide
```

<400> SEQUENCE: 8
aatggcggaa gggaggagga                                                    20

<210> SEQ ID NO 9
<211> LENGTH: 3011
<212> TYPE: PRT
<213> ORGANISM: Trypanosoma cruzi

<400> SEQUENCE: 9

```
Met Asp Arg Lys Gln Arg Ile Ile Lys Tyr Gly Ser Leu Val His Phe
 1               5                  10                  15

Ser Cys Glu Glu Gly Tyr Ile Ala Ala Ser Gly Leu Glu Ala Glu Asp
            20                  25                  30

Leu Phe Ile Arg Glu Lys Asn Asp Thr Asp Ile Asp Glu Glu Pro Leu
        35                  40                  45

Pro Leu Leu Gly Phe Glu Thr Ser Val Phe Arg Ile Glu Ala Pro Ala
    50                  55                  60

Ser Ser Leu Ala Ala Lys Ala Gln Glu Ala Val Ala Asp Arg Phe Ser
65                  70                  75                  80

Asn Asn Asn Thr Leu Leu Met Glu His Phe Ser Asn Ile Asn Thr Ala
                85                  90                  95

Pro Glu Leu Met Tyr Gly Lys Pro Phe Leu Leu His Ser Val Ser
            100                 105                 110

Gln Met Cys Val Ala Val Phe Pro Ser Lys Pro Ser Lys Ser Asp Pro
        115                 120                 125

Asn Cys Val Arg Leu Val Leu Val Lys Ala Gly Glu Val Glu Ser Asp
    130                 135                 140

Phe Cys Glu Phe Val Val Thr Pro Arg Tyr Lys Ile His Asp Asp Gly
145                 150                 155                 160

Asp Pro Val Cys Arg Gly Asp Glu Val Leu Leu Arg Leu Ala Ala Phe
                165                 170                 175

Pro Ile Phe Val His Val Thr Gly Arg Lys His Pro Gly Leu Asn Thr
            180                 185                 190

Trp Gly Met Pro Ser Glu Glu Asp Gly Cys Asp Ser Ser Ile Asn Ala
        195                 200                 205

Phe Glu Lys Gly Leu Ala Ala Gly Arg Met Val Asp Asp Leu Arg Ser
    210                 215                 220

Glu Val Asn Gly Ser Glu Glu Arg Ala Val Gly Phe Val Val Gln Arg
225                 230                 235                 240

Tyr Asp Ile Gly Arg Asp Gln Ala Asn Tyr Gln Arg Ala Leu Tyr His
                245                 250                 255

Ile Ala Arg Pro Tyr Val Pro Ser Gly Val Pro Val Leu Leu Tyr His
            260                 265                 270

Arg Glu Arg Glu Ser Phe Leu Thr Thr Ser Leu Thr Ser Gln Pro Arg
        275                 280                 285

Gln Gln Lys Glu Ser Glu Glu Asn Lys Lys Thr Met Glu Ala Asn Val
    290                 295                 300

Val Ser Gly Gly Asp Asn Gly Ile Ser Gly Gly Ala Leu Leu Thr Asn
305                 310                 315                 320

Lys Glu Ser Ser Phe Val Glu Gly Val Phe Val Ser Arg Ser Ala Thr
                325                 330                 335

Gln Leu Glu Gly Ser Gly Ile Ser Thr Leu Asp Thr Pro Asp Ala Asn
            340                 345                 350

Asp Asn Thr Asp Gly Asp Val Asp His Thr Gly Thr Pro Phe Pro Leu
```

355                 360                 365
Leu Met Lys Asp Glu Thr Ser Thr Gly Cys Val Ser Asn Glu Gly Thr
            370                 375                 380

Ala Leu Asn Asp Phe Trp Arg Ser Cys Thr Ala Leu Trp Ile Leu Glu
385                 390                 395                 400

Asn Glu Asn Pro Thr Ile Gly Gly Ala Val Arg Met Arg Ser Val Lys
                405                 410                 415

Tyr Arg Leu Arg Gln Ala Cys Ser Asn Met Tyr Leu Ala Val Ala Gly
            420                 425                 430

Ser Gly Val Asp Ala Phe Phe Glu Gly Asn Gly Glu Ser Asp Phe Ser
            435                 440                 445

Glu Thr Val Asp Gly Met Gly Ala Ala Leu Glu Glu Gly Gly Asp
            450                 455                 460

Ala Gly Ser Asn Ser Ser Arg Asn Gln Leu Arg Ala Ala Ser Leu Cys
465                 470                 475                 480

Met Ile Pro Pro Arg Thr Ala Lys Asp Ser Gln Arg Thr Leu Phe
            485                 490                 495

Thr Leu Thr Pro Met Phe Phe Thr Glu Cys Asn Phe Leu Ile Glu Asn
                500                 505                 510

Asp Cys Leu Thr Leu Gln Asn Val Leu Thr Gly Met Tyr Val Cys Thr
            515                 520                 525

Gln Glu Ala Arg Asp Arg Leu Phe Leu Gln Trp Gln Pro Ser Val Ser
            530                 535                 540

Asp Thr Ile Thr Val Arg Ser Ser Arg Gln Glu Ile Val Gln Asp Val
545                 550                 555                 560

Met Phe Leu Arg Ser His Cys Glu Arg Leu Cys Arg Tyr Arg Asp Ala
                565                 570                 575

Phe Gln Ala Leu Ala Arg Leu Lys Asn Ser Arg His Pro Ser Phe His
            580                 585                 590

Arg Asp Gly Gly Gly Leu Glu Pro Tyr Pro Gly Lys His Glu Ser Ser
            595                 600                 605

Asp Ser Cys Glu Glu Asn Leu Thr Pro Thr Arg Ala Ala Phe Val Gln
            610                 615                 620

Gly Gly Ala Leu Ser Thr Asp Phe Ala Val Ser Ser Leu Gly Arg Gln
625                 630                 635                 640

Thr Arg Thr Thr Glu Thr Pro Tyr Ala Ala Ile Leu Pro Val Ile Tyr
                645                 650                 655

Ala Ser Gln Ser Ser Leu Glu Glu Leu Ile Arg Phe Cys Ser Leu Ala
            660                 665                 670

Arg Val His Asp Ala Leu Arg Leu Asp Gly Ile Pro Ile Val Arg Arg
            675                 680                 685

Gln Arg Met Ile Phe Glu Leu Asn Ile His Arg Leu Val Met Asp Val
            690                 695                 700

Ile Leu Thr Pro Phe Ser Leu Leu Gln Ser Glu Glu Thr Asp Gly Met
705                 710                 715                 720

Gly Asp Lys Thr Met Ser Gly Met Leu Pro Trp Gly Cys Ser Pro Arg
                725                 730                 735

Leu Pro Pro Leu Pro Leu Met Gly Gly Phe Cys Met Gly Val Ala
            740                 745                 750

Leu Asp Asp Ala His Ser Glu Val His Leu Val Cys Arg Leu Ala Phe
            755                 760                 765

Arg Phe Leu Arg Gln Met Val Arg Lys Ala Lys Met Leu Lys Lys Trp
770                 775                 780

```
Leu Val Glu Phe Ile Pro Tyr Phe Leu Glu Leu Gly Tyr Arg Phe
785                 790                 795                 800

Arg Val Ser Asp Thr Met Thr Glu Leu Phe Ser Glu Asn Asn Ser Val
            805                 810                 815

Pro Arg Pro Val Val Glu Ser Val Ala Asp His Phe Ile Gly Ser Leu
        820                 825                 830

Arg Arg Gly Arg Ser Ala Gly His Leu Asn Leu Leu Ser Ser Met Cys
            835                 840                 845

Thr Val Gly Phe Ser Gly Ile Phe Glu Arg Gln Ala Met Val Cys Gln
850                 855                 860

Lys Leu Leu Val Glu Asn Ser Glu Leu Leu Ser Arg Phe Val Leu Asn
865                 870                 875                 880

Gln Asn Gly Glu Trp Ala Val Val Asn Glu Gly Glu Ala Pro Val
                885                 890                 895

Glu Cys Gly Ala Leu Phe Glu Leu Thr Arg Pro Gln Asn Ser Gln Gln
            900                 905                 910

Gln Leu Gly Ser Asp Ala Lys Tyr Ala Arg Phe Leu Gln Ser Glu Ile
        915                 920                 925

Gln Leu Leu Gly Cys Leu Cys Phe Asp Gly Cys Pro Ser Met Cys Cys
    930                 935                 940

Ala Glu Val Gly Arg Val Phe Pro Pro Glu Val Leu Leu Arg Ala Ile
945                 950                 955                 960

Gln Thr Phe Val Trp Thr Gly Ala Glu Val Met Gly Ser Pro Ser Pro
                965                 970                 975

Leu Asp Leu Leu Arg Gly His Ile Leu Arg Leu Ala Val Gln Cys Tyr
                980                 985                 990

Ile Met Pro Arg Ile Asp Asp Pro  Ala Val Gln Leu Arg  Ala Ser Thr
        995                 1000                 1005

Val Leu Phe Gly Ser Ser Ser  Leu Arg Leu Arg Glu  Glu Thr His
    1010                1015                1020

Leu Pro Ile Ser Gly Lys Pro  Asp Asp Leu Ile  Ser Ser Val
    1025                1030                1035

Lys Ala Ala Ala Leu Asn Ile  Ile Arg Ala Asn Pro  His Phe Val
    1040                1045                1050

Gln Ser Asp Met Ser Arg Ser  Val Leu Leu Arg Val  Ser Ile Asn
    1055                1060                1065

Ala Trp Leu Arg Leu Val Lys  Ala His Gln Ile Ser  Val Gln Glu
    1070                1075                1080

Met Cys Asp Leu Ile Pro Pro  Leu Leu Gly Leu Leu  Asp Gly Thr
    1085                1090                1095

Lys Asp Ile Val Asp Asp Asn  Ala Ser Arg Val Ala  Ala His Thr
    1100                1105                1110

Leu Thr Arg Leu Glu Val Ser  Glu Ala Ser Val Gln  Val Met Glu
    1115                1120                1125

Thr Arg Glu Met Ile Cys Asn  Thr Leu Gln Leu  Leu Glu Thr
    1130                1135                1140

Val Ser Asn Arg Val Ala Asp  Asn Ile Ile Leu Leu  Leu Tyr Asp
    1145                1150                1155

Ala Phe Val Lys Gly Gly Ser  Phe Pro Arg Arg Lys  Met Phe Val
    1160                1165                1170

Leu Leu Asp Phe Asp Glu Glu  Pro Val Leu Asp Ala  Lys Tyr Asp
    1175                1180                1185
```

-continued

```
Leu His Val Trp Pro Ser Glu Gly Gln Ala Leu Leu Cys Glu Lys
    1190                1195                1200

Gly Thr Gly Leu Leu His Arg Val Arg Gly Lys Tyr Gln Ser Val
    1205                1210                1215

Asp Ile Thr Asp Glu Ala Gln Glu Met Asp Ser Asn Arg Ile Asp
    1220                1225                1230

Ser Lys Glu Val Val Glu Leu Leu Gly Arg Val Cys Lys Ser Ile
    1235                1240                1245

Met Leu Arg Phe Arg Val Lys Glu Leu Val Pro Leu Leu Met Asp
    1250                1255                1260

Leu Thr Arg Tyr Glu Ser Gln Gln Leu Thr Ala Arg Ala Thr Glu
    1265                1270                1275

Leu Leu Ile Arg Leu Cys Val Val Lys Arg Thr Val Ala His Arg
    1280                1285                1290

Val Leu Gln Val His Thr Leu Pro Ser Ser Glu Val Val Arg Ser
    1295                1300                1305

Phe Asp His Leu Tyr Thr Val Ala Val Asn Thr Leu Thr Leu Glu
    1310                1315                1320

Arg Arg Gly Cys Phe Asp Glu Ala Ile Ala Phe Ala Leu Ser Asn
    1325                1330                1335

Ile Glu Glu Pro Glu Gly Thr His Asp Asp Ser Val Pro Ser Glu
    1340                1345                1350

Glu Leu Glu Glu Glu Tyr Leu Ile Glu Asp Asp Gly Ser Asp Asp
    1355                1360                1365

Glu Ala Gly Gly Asp Asp Gly Gly Ala Gly Ala Asp Gln Ala Gly
    1370                1375                1380

Lys Glu Ala His Gly Gly Arg His Leu Trp Gly Lys Thr Ala Gly
    1385                1390                1395

Ala Val Arg Val Leu Ala Tyr His Asn Ala Val Arg Arg Arg Arg
    1400                1405                1410

Arg Ser Val Gly Leu Ser Glu Asn Ser Glu Leu Pro Leu Arg Leu
    1415                1420                1425

Ile Val Arg Met Glu Leu Val Cys His Trp Gly Ile His Ile Pro
    1430                1435                1440

Leu Met Arg Met His Ala Ser Ile Asp Pro Asn Ser Arg Ala Phe
    1445                1450                1455

Phe Gln Trp Met Arg Phe Phe Tyr Leu Phe Thr Phe Val Arg Gly
    1460                1465                1470

Asn Ala Arg Lys Leu Leu Gly Ser Ile Asp Leu Phe Met Arg Ser
    1475                1480                1485

Leu Asn Leu Lys Lys Glu Cys Thr Val Met Cys Leu His Ile Ile
    1490                1495                1500

Val Ala Ile Phe Ala Ser Val Ala Asp Pro Thr Pro Tyr Leu Ser
    1505                1510                1515

Asn Thr Phe Leu Thr Glu Cys Val Lys Tyr Leu Asp Ser Glu Val
    1520                1525                1530

Ser Thr Arg His Ala Asp Val Asp Phe Leu Ser Arg Leu Ser Asn
    1535                1540                1545

Tyr Val Phe Ser Asn Pro Ala Val Gly Gly Val Pro Arg Arg Arg
    1550                1555                1560

Met Met Gln Leu Leu Arg Asp Tyr Asn Ile Leu Arg Cys Leu Pro
    1565                1570                1575

Arg Pro Gly Gly Val Gln Val Ser Pro Val Arg Cys Asp Phe Ile
```

-continued

```
            1580                1585                1590
Ala Ser Met Val Glu Leu Leu Cys His Ile Cys Asn Cys Pro Thr
    1595                1600                1605
Ser Ala Leu Ala Met Gly Gln Arg Ala Leu Pro Met Gln Asp Ile
    1610                1615                1620
Phe Ala Ile Ile Leu Glu Tyr Gly Ser Leu Tyr Ser Pro Leu His
    1625                1630                1635
Arg Lys Ser Tyr His Gln Arg Asp Glu Leu Glu Arg Lys Gln Phe
    1640                1645                1650
Gln Leu Val Gly Thr Tyr Leu Arg Ala Leu Val Leu Leu Tyr Ile
    1655                1660                1665
Thr Ala Glu Arg Glu Glu Gly Gly Gln Gly Lys Glu Met Ile Lys
    1670                1675                1680
Leu Glu Trp Met Ala Asn Arg Glu Trp Trp Ala Val Val Glu Met
    1685                1690                1695
Leu Thr Arg Gln Leu His Gly Ile Thr Glu Leu Ile Leu Thr Asn
    1700                1705                1710
Lys Gly Lys Val Val Asn Arg Gly Ile Arg Val Ile Gln Arg Tyr
    1715                1720                1725
Arg His Val Trp Leu Met Ser Leu Pro Val Ala Leu Leu Thr Phe
    1730                1735                1740
Phe Ser Ala Cys Phe Ser Glu Ala Gly Phe Tyr Arg Tyr Gln Asp
    1745                1750                1755
Ser Val Gly Val Thr Phe Ala Val Met Cys Ser Ser Leu Met Glu
    1760                1765                1770
Phe Ser Ser Asn Leu Ile Ser Asn Ser Asp Ala Leu Glu Leu Ser
    1775                1780                1785
Val Gln Glu Ala Val Asn Tyr Arg Arg Leu Leu Gly Leu Leu His
    1790                1795                1800
Met Gln Thr Ala Asn Ile Val Gly Leu Glu Thr Leu Ser Ser Gln
    1805                1810                1815
Leu Glu Ile Val Arg Asp Gln Ile Leu His Trp Leu Leu Gln Arg
    1820                1825                1830
Glu Arg Leu Ser Lys Ala Glu Arg Gln Gly Gln Gly Gly Gly Trp
    1835                1840                1845
Glu Glu Arg Ala Arg Ser Ser Asp Phe Asp Glu Tyr Ser Ser Pro
    1850                1855                1860
His Asp Thr Leu Ala Ile Gly Glu Gly Val Ser Gln Arg Ile Gln
    1865                1870                1875
Asp Ser Leu Gly Asp Ser Phe Ser Ala Arg Leu Phe Leu Ser Ser
    1880                1885                1890
Gly Val Ser Arg Cys Arg Glu Leu Glu Ala Thr Arg Ser Ala Leu
    1895                1900                1905
Arg Thr Phe Val Lys Ser Asp Val Leu Ile Pro Ile Glu Asp Ser
    1910                1915                1920
Leu Glu Ile Gly Glu Ala Ala Asn Val Val Asn Ala Leu Leu Cys
    1925                1930                1935
Arg Ser Ser Ala Leu Ser Gly Val Arg Gly Phe Val Trp Ser Ala
    1940                1945                1950
Leu Asp Gly Met Arg Lys Arg Tyr Phe Ser Pro Met Ala Leu Val
    1955                1960                1965
Gly Leu Leu Asn Leu Phe Tyr Asn Ala Leu Tyr Ala Ser Phe Tyr
    1970                1975                1980
```

```
Val Lys Glu Ser Pro Pro Leu Gln Ala Ala Glu Gly Ala Gly Lys
    1985                1990                1995

Asn Ser Thr Glu Arg Glu Asp Thr Trp Asn Leu Leu Gln Leu Thr
    2000                2005                2010

Phe Thr Asp Leu Gly Met Ser Asn Val Val Ala Ser Leu Ser Val
    2015                2020                2025

Lys Asp Asp Asp Val Ile Thr Tyr Ser Ser Ile Arg Leu Ser Val
    2030                2035                2040

Met Leu Leu Glu Gly Gly Asn Thr Arg Ala Gln Tyr Ala Leu Leu
    2045                2050                2055

Lys Asp Phe Gly Ala His Gln Val Arg Phe Phe His Asn Ile Arg
    2060                2065                2070

Glu Leu Leu Gln Lys Ser Leu Gln Trp Val Arg Gln Ile Asn Leu
    2075                2080                2085

Gln Gln Gln Leu Val Ile Leu Glu Cys Gly Gly Thr Pro Val Gly
    2090                2095                2100

Ser Asn Ser Thr Leu Phe Thr Ser Ala Leu Phe Ala Ala Val Leu
    2105                2110                2115

Lys Ser Ser Ser Tyr Arg Lys Lys Ser Glu Arg Asn Gly Gly Lys
    2120                2125                2130

Glu Lys His Ile Leu Gly Trp Asp Arg Val Glu Gly Cys Met Arg
    2135                2140                2145

Leu Arg Leu Leu His Ala Leu Phe Arg Met Leu Gln Leu Phe Cys
    2150                2155                2160

Glu Gly His Asn Leu Gly Met Gln Asn Tyr Ile Arg Phe Gln His
    2165                2170                2175

Asp Asn Met His Ser Val Asn Ile Val His Glu Val Leu Leu Leu
    2180                2185                2190

Leu Ala Glu Leu Ser Gly Met Thr His Gly Ala Thr Val Asp Val
    2195                2200                2205

Ile Arg Gly Gly Phe Glu Leu Leu Thr Glu Leu Cys Gln Gly Pro
    2210                2215                2220

Cys His Glu Asn Gln Thr Ala Leu Leu Ser Tyr Asp Val Cys Val
    2225                2230                2235

Thr Met Cys Gly Leu Leu Asp Val Leu Ser Lys Leu Glu Ile Ile
    2240                2245                2250

Gly Thr Arg Thr Ala Pro Glu Asn Asn Ser Arg Asn Met Asn Thr
    2255                2260                2265

Glu Met Gly Ile Thr Asn Thr Thr Asn Thr Asn Gly Thr Arg Leu
    2270                2275                2280

Thr Glu Ser Phe Met Asn Gly Val Val Ser Gln Arg Gly Leu Lys
    2285                2290                2295

Leu Thr Arg Lys Ala Val Asp Cys Leu Arg Val Ser Leu Thr Thr
    2300                2305                2310

Phe Leu Leu Ser Leu Ile Glu Gly Cys Arg Ser Pro Glu Thr Phe
    2315                2320                2325

Arg Arg Val Leu Ala Gln Ile Pro Ile Glu Ile Glu His Gln
    2330                2335                2340

Leu Ser Ile Ala Thr Pro Glu Met Cys Asp Arg Ile Leu Glu Asp
    2345                2350                2355

Glu Thr Leu Glu Asp Asp Pro Thr Val Ala Ala Leu Phe Asn Trp
    2360                2365                2370
```

-continued

```
Leu Ile Phe Leu His Ile Val Arg Pro Phe Ala Asp Gly Leu Tyr
2375                2380                2385

Leu Gln His Ile Asp Glu Leu Leu Arg Arg Thr Thr Arg Leu Arg
2390                2395                2400

Glu Arg Leu Gly Arg Ile Glu Ile Arg Arg Asp Asp Gly Leu Leu
2405                2410                2415

Glu Lys Val Phe Phe Cys Ile Pro Ser Ile Cys Arg Gly Leu Ser
2420                2425                2430

Gln Asn Ile Lys Asp Asp Val Leu Trp Ser Val Asn Arg Thr Ser
2435                2440                2445

Arg Ala Thr Lys Leu Gly Asp Phe Leu His Gln Ser Asp Asn Leu
2450                2455                2460

Ile Phe Glu Val Glu Arg Ala His Asp Phe Gln Arg Trp Val Ala
2465                2470                2475

Arg Trp Thr Arg Phe Thr Leu Thr Thr Ile Asp Thr Ala Val Glu
2480                2485                2490

Lys Glu Asn Glu Met Asp Thr Glu Gly Val Met Glu Glu Lys Lys
2495                2500                2505

Val Arg Phe Tyr Ser Leu Lys Lys Cys Trp Asn Arg Phe Met Ala
2510                2515                2520

Pro Phe Ile Phe Ser Ser Gln Leu Ser Tyr Tyr Glu Tyr Ala Ser
2525                2530                2535

Ile Leu Phe Ala Val Leu Ile Asn Ile Gly Leu Ile Ser Val Glu
2540                2545                2550

Gly Ala Lys Trp Asp Trp Ala Thr Val Gln Val Ser Lys Leu Ala
2555                2560                2565

Ile Thr Cys Leu Cys Val Leu Gln Phe Val Leu Ser Cys Val Thr
2570                2575                2580

Leu Cys Met Asp Ala Val Val Phe Phe Pro Ala Cys Leu Tyr Lys
2585                2590                2595

Glu Tyr Arg Arg Lys Glu His Met Arg Leu Gly Ile Ala Lys Leu
2600                2605                2610

Asn Ala Thr Met Arg Glu Val Phe Asp Gly Leu Thr Lys Gly Glu
2615                2620                2625

Val Val Tyr His Phe Leu Thr Arg Phe Thr Ile Gln Phe Arg Leu
2630                2635                2640

Phe Leu Val Val Thr Ala Ala Leu Ser Leu Leu Val Ser Arg Tyr
2645                2650                2655

Phe Ala Ala Ala His Leu Leu Phe Val Ile Tyr Lys Val Pro Thr
2660                2665                2670

Leu Cys Thr Phe Ile Asn Ala Ile Thr Gln Asn Gly Lys Gln Leu
2675                2680                2685

Leu Leu Thr Ala Phe Leu Gly Val Val Leu Tyr Leu Phe Ala
2690                2695                2700

Ile Val Gly Tyr Leu Leu Phe Pro Arg Gln Phe Asp Ser Ser Asp
2705                2710                2715

Gly Pro Glu Asn Gly Asn Cys Val Asn Leu Phe Arg Cys Phe Leu
2720                2725                2730

Phe Ile Leu Trp Gln Gly Leu Arg Gln Gly Gly Gly Val Gly Asp
2735                2740                2745

Ile Met Gln Glu Glu Ser Trp Ser Ser Ser Thr Leu Phe Pro Arg
2750                2755                2760

Val Ser Tyr Asp Leu Val Phe Phe Ala Leu Val Asn Val Val Phe
```

| | | | | | | | | | |
|---|---|---|---|---|---|---|---|---|---|
| | | 2765 | | | 2770 | | | 2775 | |
| Leu | Asn | Ile | Met | Phe | Gly | Leu | Ile | Ile | Asp | Thr | Phe | Gly | Glu | Leu |
| | 2780 | | | | | 2785 | | | | 2790 | | | | |
| Arg | Asp | Ala | Lys | Arg | Glu | Lys | Glu | Leu | Asp | Met | Lys | Ser | Thr | Cys |
| | 2795 | | | | | 2800 | | | | 2805 | | | | |
| Phe | Val | Cys | Gly | Leu | Glu | Ala | Asp | Glu | Phe | Glu | Arg | Ala | His | Val |
| | 2810 | | | | | 2815 | | | | 2820 | | | | |
| Gly | Gly | Phe | Arg | Ala | His | Val | Val | His | Glu | His | Asn | Met | Trp | Met |
| | 2825 | | | | | 2830 | | | | 2835 | | | | |
| Tyr | Phe | Tyr | Phe | Met | His | Tyr | Leu | Arg | Arg | Lys | Asp | Pro | Asn | Asp |
| | 2840 | | | | | 2845 | | | | 2850 | | | | |
| Phe | Thr | Gly | Gln | Glu | Ser | Tyr | Val | Asp | Glu | Arg | Ile | Arg | Arg | Gly |
| | 2855 | | | | | 2860 | | | | 2865 | | | | |
| Asp | Leu | Gly | Phe | Phe | Pro | Glu | Asp | Ser | Leu | Ser | Leu | Gly | Asn | |
| | 2870 | | | | | 2875 | | | | 2880 | | | | |
| Gly | Gly | Arg | Glu | Glu | Asp | Ala | Ala | Gly | Ala | Gln | Lys | Asp | Val | |
| | 2885 | | | | | 2890 | | | | 2895 | | | | |
| Ser | Gly | Met | Asp | Glu | Glu | Gly | Cys | Ala | Thr | Arg | Pro | Gly | Arg | Glu |
| | 2900 | | | | | 2905 | | | | 2910 | | | | |
| Lys | Ala | Pro | Ala | Ala | Gly | Ser | Gly | Ala | Ala | Asn | Gly | Gln | Glu | Val |
| | 2915 | | | | | 2920 | | | | 2925 | | | | |
| Ala | Leu | Thr | Leu | Lys | Glu | Leu | Ala | Gly | Val | Lys | Glu | Ala | Leu | Ser |
| | 2930 | | | | | 2935 | | | | 2940 | | | | |
| Ala | Phe | Val | Arg | Asp | Val | Ser | Ala | Asp | Ala | Gln | Lys | Val | Lys | Ser |
| | 2945 | | | | | 2950 | | | | 2955 | | | | |
| Leu | Leu | Gln | Gln | Leu | Glu | Ile | Met | Ser | Arg | Gly | Ala | His | Val | Met |
| | 2960 | | | | | 2965 | | | | 2970 | | | | |
| Ser | Leu | Gly | Gly | Gly | Thr | Ala | Asn | Asp | Pro | Gly | Ser | Thr | Ser | Gly |
| | 2975 | | | | | 2980 | | | | 2985 | | | | |
| Thr | Arg | Leu | Ser | Arg | Gly | Glu | Gly | Ser | Lys | Ser | Ser | Leu | Arg | Arg |
| | 2990 | | | | | 2995 | | | | 3000 | | | | |
| Ser | Ile | Gly | Glu | Gly | Ser | Lys | Asn | | | | | | | |
| | 3005 | | | | | 3010 | | | | | | | | |

```
<210> SEQ ID NO 10
<211> LENGTH: 9036
<212> TYPE: DNA
<213> ORGANISM: Trypanosoma cruzi

<400> SEQUENCE: 10
atggatcgaa agcaacgcat aattaaatac ggctctcttg tccacttctc atgcgaggaa      60
ggatatattg ctgcgtcagg actggaagct gaggacctgt tcatccgtga aaagaatgac     120
accgatatcg atgaggagcc gctgccctg ctggggtttg aaaccagcgt ctttcggatt      180
gaagcacccg cgtcaagcct tgcagcaaag gcacaagagg cggtagcgga tcgttttagc     240
aacaataaca cgcttcttat ggagcacttc agcaacatca cacggcacc ggagctcatg      300 tatgggaaac cttttcttct tttgcattcc gtcagccaga tgtgcgtggc ggtatttcca     360
tcaaaaccat ccaagagtga tcctaactgt gtgaggcttg tgcttgtgaa ggccggggag     420
gttgaatcgg acttttgtga atttgtcgtg acgccacggt acaaaattca tgacgatggg     480
gatcccgtgt gtcgcggcga tgaggttctc ctacgactgg ctgcgtttcc aattttttgta    540 cacgttacgg gaaggaaaca tccaggcttg aatacatggg gcatgccgtc gaagaagac      600 ggctgcgata gtagcatcaa cgcttttgaa aagggttgg ccgccggcag aatggtcgat     660
```

```
gacttgcgtt cagaagtaaa cggctcagag gaaagggcgg tgggtttcgt ggtgcagcgg      720
tatgacattg ggagggatca ggcaaactat caacgtgccc tttaccacat tgcccggcca      780
tacgtaccat ccggcgtgcc agtcttactt taccaccgcg agcgcgaaag ttttctcacg      840
acaagcctca cgtcacagcc aaggcagcaa aaggaatctg aggagaacaa aaaacaatg       900 gaggcgaatg ttgtgagtgg gggtgataat ggaataagcg gcggcgcctt gttaacaaac      960
aaagaaagct cttttgtgga gggtgttttt gtatcgagaa gtgccacaca gttagaaggg     1020
agcggcatct ccaccccttga tacgccggat gcaaatgata atacggacgg tgatgttgac     1080
catactggga caccgttccc gttgttgatg aaggacgaaa cttcgacggg ctgtgtttct     1140
aacgaaggga ctgccttaaa cgacttctgg cgcagttgca cggccctctg gattttggag     1200
aatgaaaatc caacgatagg gggtgccgtg cgcatgcgt ctgtgaagta tcgtcttcga      1260
caggcgtgtt caaacatgta tttggcggtt gctggctctg tgttgacgc attttttgaa      1320 ggtaatggag aaagcgattt ttcagaaacg gtcgatggta tgggcgcggc ggcgttagaa     1380
gagggcggtg atgcaggcag caacagtagc cggaatcaat tgagggccgc ctcactctgt     1440
atgataccac caccacgcac cgcgaaggat tcgcaacgca ctctctttac gttaactccc     1500
atgtttttta ccgaatgcaa cttctcttatt gagaatgatt gcttgacgct tcaaaatgtg     1560
ttaacaggaa tgtatgtatg cacacaagag gcgagagacc gccttttttct ccagtggcaa    1620 ccatctgtct ctgataccat cactgtgcgg agttctcgtc aagagattgt gcaggatgtc     1680
atgtttctga ggtcacactg cgagagactc tgccggtatc gtgatgcctt ccaggctttg     1740
gcacgcttaa aaaattcgcg acatccgtct tttcatcggg atggtggagg cttggaacca     1800
tatcccggaa acacgagag ttccgactca tgtgaggaaa atttaacgcc tacgagggcg      1860
gcatttgtgc agggcggcgc tctttcgaca gattttgctg tttccagttt agggcgtcaa     1920
acgaggacta ctgagactcc gtacgcagcg attctccccg tcatttatgc ctctcagagt     1980
agtttggagg aactcattcg tttctgttcg ttagctcgcg tgcatgacgc tctccgtctt     2040
gacggtattc cgatcgtgcg gcgtcagcgg atgatatttg agttaaatat ccaccggctt     2100
gttatggacg tcattctcac gcccttttcc ctgctacagt cggaggaaac ggatggaatg     2160
ggggataaaa ccatgagtgg aatgctccca tggggctgca gcccacgatt gccaccgttg     2220
cctctcatgg gtggttttttt ttgcatgggc gttgcgttgg atgatgcaca ttcagaggtg     2280
caccttgttt gtcgcctcgc ctttcgattc ttacgtcaga tggtgcgcaa ggcaaagatg     2340
ctgaagaagt ggcttgttga attcatccca tactttttgg aacttggggg ttaccgcttt     2400
cgtgtgtctg acacaatgac ggagctgttt tcagaaaaca acagcgttcc aagaccagtt     2460
gtggagtctg tggcggacca cttcattgga tctcttcgcc gcgacgcag tgcaggtcat       2520 ttgaatctat tgtcctccat gtgcaccgta ggatttagcg gtatctttga gagacaagcc     2580
atggtgtgcc agaagcttct tgttgaaaac agcgaattgc tttctcgttt tgtgctgaat     2640
caaaatgggg aatgggcggt tgtggtgaat gagggtgaag ctcctgtcga gtgcggtgcc     2700
ctttttgaat tgacgcggcc ccagaattcc cagcagcagc tgggctccga tgcgaaatat     2760
gccaggtttt tacagagtga aattcaattg cttggctgtt tgtgctttga cggctgtccc     2820
tccatgtgct gtgcggaggt ggggagggtg ttcccaccag aggtgctgct tagggccatc     2880
caaacatttg tctggaccgg cgccgaggtg atgggtctc ccagccctttt ggatctgctg     2940 cgcgggcata tcttgcggct tgccgtgcag tgttacatca tgcctcgtat tgacgacccc     3000
```

-continued

```
gcggtgcagt tgcgggcgag tacagtgctg tttggctcca gctctcttcg tctgagggag    3060
gagacgcatc tgcccatctc cggcaaacct gacgacgacc tcatttcttc agtgaaagcg    3120
gccgcgctca acatcattcg tgccaatcca cactttgtac agtctgatat gagtcgaagc    3180
gtgctgctac gcgtgtcgat aaacgcatgg ctacggttgg tgaaggccca ccagatatct    3240
gtgcaggaga tgtgtgacct tatccccca ctgctaggcc ttctggacgg caccaaggac     3300
atcgttgacg acaatgccag cagggtcgcc gcgcacactc tcacgcct tgaggtgtcc      3360
gaggcaagcg tgcaagtgat ggaaacacgt gagatgatct gcaatacact ccttcagctc    3420
ctggagactg tgtcaaaccg tgtggcagac aacataatat tgctcctcta cgacgccttt    3480
gtcaagggtg gcagttttcc acgccgaaaa atgttcgttc tgttggattt tgacgaagag    3540
cccgtccttg acgcgaaata tgatttgcat gtgtggccca gcgaggggca ggccctgcta    3600
tgtgagaagg gcacaggcct tctccaccga gtccggggta aatatcagtc tgttgacata    3660
accgatgagg cgcaggagat ggacagtaac cgcatcgact caaggaggt tgtggagctg     3720
ttgggacgtg tgtgtaaaag tatcatgttg cggtttcgcg tgaaggaact tgtcccgctg    3780
ctcatggatc ttacccgcta tgaaagccag caactaacag cacgggcaac agagttgctg    3840
attcgccttt gtgtggtgaa gcgaaccgtg gcgcaccgtg tgctgcaggt gcatacgtta    3900
ccctcttctg aggttgtacg tagttttgac cacctctaca ccgttgctgt gaacaccctc    3960
acgttagaac gacgtggatg ctttgatgag gccatcgcgt ttgccctctc gaatattgag    4020
gaacctgagg gaacacacga cgactccgtt ccttctgaag agttggagga ggaatatttg    4080
attgaggatg atggcagtga tgatgaggct ggtggtgatg atgggggagc tggtgcagat    4140
caggctggaa aggaggcaca cggcgggcgt catctttggg gaaaaactgc cggggctgtg    4200
cgtgtgttag cgtaccataa tgcggtgcgc cgtcgccgcc gttcagtcgg actcagcgag    4260
aattctgaat tgccgctgcg tcttattgtc cgcatggaat tggtgtgtca ttggggtatt    4320
catattccac tcatgcgaat gcacgcgagc attgatccca acagtcgagc gttcttccaa    4380
tggatgcgtt tcttttacct tttacgtttt gtgcgaggca acgcaagaaa attgctggga    4440
agcattgatt tgttcatgcg ctctcttaac cttaaaaagg agtgcaccgt catgtgtctt    4500
cacatcattg tcgccatctt tgcttccgtc gccgatccca ccccataccet cagtaacacg    4560
ttcctcacgg aatgtgtgaa atatctggat agtgaggtgt cgacgcgtca cgcagatgtg    4620
gactttcttt cgcggctgag taattatgtg ttttccaatc ccgccgtggg cggcgtgcca    4680
cggcgacgta tgatgcagct tctacgcgac tacaatatac tccgttgttt gccgcgccct    4740
ggtggggttc aggtgtcacc agtgcgatgt gattttatcg cctccatggt cgagctgctt    4800
tgtcacatct gcaactgccc gacgagcgcg ctggcgatgg gacagagagc ccttccgatg    4860
caagatatct ttgccatcat cttggagtat ggctccctct acagcccgct gcaccgcaaa    4920
agttaccatc aacgcgacga attggaacga aaacaattcc agcttgtggg tacatactta    4980
cgtgcccttg tcctactgta catcaccgct gagagggagg agggtggcca ggggaaggag    5040
atgattaagt tggagtggat ggcaaaccgc gagtggtggg ccgttgtgga gatgttaacc    5100
agacagttgc acggaatcac ggagcttatt ttaaccaata aggggaaggt ggtaaaccga    5160
gggattcgtg taatacaacg ctaccggcat gtatggctta tgtcgttacc cgtcgcattg    5220
ctgacatttt tctccgcatg cttttcagag gcgggctttt atcgatatca ggactcagtg    5280
ggagtcacct ttgcggtcat gtgcagcagc ctcatggaat tttcctccaa tcttatttca    5340
aattcggacg cccttgagtt gagtgttcaa gaggctgtga actatcgccg tcttctgggc    5400
```

```
ctgcttcata tgcagactgc taacattgtt ggattggaaa ccctctcgag tcaattggag    5460
atcgtccgcg accaaattct tcactggctg ctccagcgcg agaggttaag caaagcggaa    5520
cgacaaggac aaggtggtgg ctgggaagag agggcacgca gcagtgattt tgacgaatat    5580
tcaagcccac atgacacgct cgctattggg gagggcgtgt cccaacgcat acaggattct    5640
cttggcgatt cttttctgc gagactattt ctctccagtg gtgtatcgag atgtcgtgag    5700
ttggaggcta cacgcagtgc ccttcgtaca tttgttaaga gcgatgtatt gattccaata    5760
gaggatagct tggaaatagg cgaagccgca aatgtggtga atgcgttgct ctgtcgcagt    5820
tctgctctgt cgggtgttcg tggctttgtt tggagtgcac tggatggcat gcgaaagcga    5880
tactttagcc ccatggcgct tgtaggcctt ttgaacctt tctacaatgc tttgtatgcg    5940
agtttctatg tcaaggaatc tccgccatta caggcggcag aaggtgcagg aagaacagc    6000 acggaaaggg aggacacctg gaatcttctg cagcttacct tcacggacct tggcatgtca    6060
aatgtggttg catcactgag tgtaaaggac gatgatgtga ttacgtacag ttccattcgc    6120
ctcagtgtga tgctccttga gggtggcaac acacgggcac agtatgcact tttaaaagac    6180
tttggagcac accaagtaag attttttccat aacattcgcg agttgctgca aaaatcatta    6240
caatgggtgc ggcaaattaa cttgcagcag cagcttgtca ttttggagtg tggtgggact    6300
ccggtgggct ccaactccac acttttcaca tctgcgctgt ttgccgcggt acttaaatca    6360
tcctcgtatc ggaaaaaaag tgaacgcaat ggtgggaaag agaaacacat tttgggttgg    6420
gatcgtgtag aaggctgtat gcggttgcga cttctccacg ccttgttccg catgctgcaa    6480
cttttctgcg aaggccacaa cctcggcatg caaaattata ttcgttttcca gcacgataat    6540 atgcatagtg taaacattgt ccatgaggtc ctgttgcttc tcgcagagct ctctggaatg    6600
acgcacggtg ccacggtcga tgtgatacgt gggggttttg agttgttaac ggagttatgc    6660
cagggtccat gccacgaaaa ccagacggcg ctgctgagct acgatgtttg tgtgacgatg    6720
tgcggtcttc ttgacgtgtt gagtaaattg gagatcattg gcacccggac ggccccagaa    6780
aacaactcga ggaatatgaa tacgaaatgt ggcattacca atactactaa tactaatggt    6840
acaaggttaa ctgaaagctt catgaacggt gtcgtatcgc aacgtggtct aaagcttacc    6900
agaaaggcag ttgattgcct ccgcgtgtct ctcaccacat ttctgttgtc tcttattgaa    6960
ggatgccgct cccctgaaac cttccgccgt gttcttgcac agattcccat tgaaatcatt    7020
gaacaccagc tttccatcgc taccccggag atgtgcgatc gtattcttga ggatgagacg    7080
cttgaggatg atccgactgt tgcggcactc ttcaactggc tcatctttct tcatattgtg    7140
cggccctttg cggatgggct ctacctgcaa cacattgatg agttgctgcg tcgcaccacg    7200
aggcttaggg agcgtcttgg ccgtattgag atacgacggg acgatgggtt gcttgagaag    7260
gtcttttttt gcatcccttc aatttgtcgc ggactctctc agaacattaa ggacgatgta    7320
ctctggagcg tcaatcgcac aagtcgggcg acgaagttgg gcgatttttt acatcagagc    7380
gataacttga tctttgaggt ggagagggcg catgacttcc agcgctgggt ggcgcggtgg    7440
acgcgattta ctttgaccac catcgacacc gccgtagaga aggagaatga aatggatacg    7500 gaggggtga tggaagaaaa aaaggttcga ttctactcgt taaagaagtg ctggaatcgt    7560
tttatggcac catttatctt ttcctcccaa ctctcttatt acgaatatgc ctccatccta    7620
ttcgcagtgc ttattaacat tggactcatc tcggttgagg gggcgaagtg ggattgggcc    7680
acggtgcaag tttcaaaact cgccatcacg tgtctttgcg tcctacagtt tgtgctttcc    7740
```

```
tgtgtgactt tatgcatgga cgccgtcgtg ttttttcctg catgcctgta caaggagtac    7800
aggcggaaag aacacatgag gttgggaatt gccaagctga atgcgacgat gcggaggtc     7860
tttgatggac taacaaaagg agaagtggtg taccacttcc ttacacgctt tacgattcag    7920
tttcgtcttt ttcttgttgt gacggcggcg ttgagccttt tggtgtcgcg gtactttgct    7980
gccgcccacc ttcttttttgt tatctacaaa gtgcccaccc tatgtacctt catcaacgcc   8040
attacgcaga atgggaaaca gctcctgttg acagcctttc ttggggttgt cgtgttgtac    8100
cttttttgcca ttgttggcta ccttcttttt ccgcggcagt ttgacagctc ggatggacca   8160
gaaaacggga actgcgtcaa tctctttcgg tgctttttat tcattctctg gcagggactt    8220
cgacagggtg gtggtgttgg cgacatcatg caggaggagt catggtcgag tagcactctt    8280
tttccacgtg tcagttacga tttggttttc tttgctcttg ttaatgtcgt gtttctgaac    8340
atcatgtttg gtctcatcat tgacacattt ggcgagttgc gtgacgccaa acgtgagaag    8400
gagctcgaca tgaaaagcac atgttttgtg tgtggcctgg aggcagacga atttgaaagg    8460
gcccatgtcg gaggattcag ggcgcatgta gtgcatgagc ataacatgtg gatgtatttc    8520
tactttatgc actacctgcg gcgcaaggac ccaaacgatt tcaccgggca ggagtcgtat    8580
gttgatgaaa ggattcggcg aggtgatctt ggcttcttcc cagaggagga ctctcttttcc   8640
ctggggaatg gcggaaggga ggaggacgct gcggctggtg cacagaaaga tgtctcaggg    8700
atggacgagg agggatgtgc cacacggccg ggacgtgaga aggcaccggc ggcggggagt    8760
ggagcggcga acggccagga agtggcgctg acgctcaagg agctggctgg tgtgaaggag    8820
gcgctcagtg catttgtccg tgacgtgagt gcggatgctc agaaggtgaa gtcattgctt    8880
caacagctgg aaatcatgag tcgcggtgct catgtcatgt cccttggcgg aggcacagcg    8940
aatgacccag gatctacctc cggcacacgt cttagcagag ggagggggtc gaaaagttca    9000
ctgcgacgct ccataggaga aggcagcaaa aattaa                              9036
```

<210> SEQ ID NO 11
<211> LENGTH: 3099
<212> TYPE: PRT
<213> ORGANISM: Trypanosoma brucei

<400> SEQUENCE: 11

Met Ser Gln Ser Arg Val Pro Ile Arg Tyr Gly Ala Phe Ile His Leu
1               5                   10                  15

Ser Cys Asp Glu Gly Tyr Val Thr Ala Gly Gly Leu Gly Asn Glu Gly
            20                  25                  30

Leu Phe Ile Arg Asn Lys Asn Glu Leu Ser Asp Asp Ala Glu Pro Leu
        35                  40                  45

Pro Leu Phe Gly Phe Glu Thr Ser Val Phe Gln Ile Leu Pro Pro Thr
    50                  55                  60

Val Ala Lys Val Ala Ala Glu Glu Gly Leu Ser Lys Gly Asn Arg Ala
65                  70                  75                  80

Pro Asn Ser Asn Pro Leu Ser Asp Gly Val Ser Asn Ile Tyr Ser Thr
                85                  90                  95

Gln Gln Val Thr Phe Gly Gln Leu Phe Val Leu Val His Ala Val Ser
            100                 105                 110

Arg Leu His Val Ala Ala Leu Pro Ser Glu Pro Ser Glu Arg Asp Pro
        115                 120                 125

Asp Cys Ala Arg Leu Val Leu Ala Pro Pro Gly Glu Ile Glu Gln Thr
    130                 135                 140

```
Phe Cys Gln Phe Ile Phe Thr Pro Arg Tyr Thr His Gly Glu Gly
145                 150                 155                 160

Asp Val Val Cys Arg Gly Asp Glu Val Leu Val Gln Leu Ala Ser Ile
            165                 170                 175

Pro Ile Phe Leu Gln Thr Thr Val Val Ser Pro Thr Arg Pro Val Lys
                180                 185                 190

His Glu Thr Phe Gly Ser Ala Ser Phe Pro Tyr Glu Pro Thr Asp Gly
            195                 200                 205

Cys Gly Arg Gly Asn Ser Trp Ser Ala Gly Thr Arg Met Ala Leu Ser
    210                 215                 220

Ala Val Leu Gly Ala Pro Glu Val Asn Leu Ser Glu Ala Lys Ala Leu
225                 230                 235                 240

Val Phe Val Val Glu Arg Tyr Asp Ile Asp Arg Asp Lys Ala Glu His
            245                 250                 255

Gln Arg Ile Leu His Arg Ile Pro Arg Pro Cys Val Ser Ala Gly Val
        260                 265                 270

Pro Val Ile Phe Tyr His Leu Glu His Lys Arg Val Leu Ala Thr Ser
            275                 280                 285

Val Ala Met Pro Pro Cys Gln Gly Gly Lys Ile Gly Val Ser Gly
290                 295                 300

Val Ala Pro Arg Gly Asn Glu Gly Gly Glu Arg Asp His Leu Leu
305                 310                 315                 320

Lys Thr Arg Gln Thr His Ser Val Met Gly Asn Val Thr Val Ile Cys
                325                 330                 335

His Ala Ser Gly Arg Phe Ala Ala Gly Ser Ser Lys Ser Gln Gly
            340                 345                 350

Ser Asp Ser His Ser Ala Gly Ala Thr Ser Leu Asp Ser Asp Pro Cys
        355                 360                 365

Ser Thr Lys Gly Lys Ala Pro Asp Asp Arg Lys Arg Val Asn Gly Val
    370                 375                 380

Gly Gly Ala Ala Leu Pro Leu Phe Ala Val Asp Lys Gly Val Ala Asp
385                 390                 395                 400

Gly Thr Phe Ser Glu Glu Gly Ala Leu Ser Gly Leu Gln Cys Ser Cys
                405                 410                 415

Thr Ala Leu Trp Ile Leu Glu Asn Glu Gln Pro Thr Val Gly Gly Ala
            420                 425                 430

Val Asn Met Asn Ser Gly Val Tyr Arg Leu Arg Gln Ala Cys Ser Asn
        435                 440                 445

Leu Tyr Val Ala Val Glu Gly Ser Ala Val Asp Thr Ile Leu Glu Gly
    450                 455                 460

Asp Gly Ser Pro Glu Gly Ser Val Val Ser Gln Arg Ser Cys Cys Asn
465                 470                 475                 480

Leu Thr Gly Asp Ile Val Asn Glu Glu Gly Gly Asp Val Val Arg Pro
            485                 490                 495

Thr Thr Leu Ser Met Ile Pro Pro Arg Thr Pro Lys Asp Leu Gln
        500                 505                 510

Arg Thr Leu Phe Arg Leu Ser Pro Met Phe Asn Thr Asp Cys Gly Tyr
    515                 520                 525

Leu Ile Glu Asn Asp Cys Leu Leu Gln Asn Val Ala Thr Asp Met
            530                 535                 540

Tyr Leu Cys Thr Ser Glu Gly Ser Glu Thr Leu Ser Leu Ser Trp Lys
545                 550                 555                 560

Pro Ser Asn Ile Asp Leu Ile Val Val Arg Arg Ala Ala Thr Asp Val
```

```
                565                 570                 575
Gln Asp Ser Val Leu Phe Leu Trp Ser Gln Cys Glu Thr Leu Ser Gly
            580                 585                 590

Tyr Arg Asp Ala Phe Gln Val Leu Thr Thr Glu Gly Thr Ala Thr His
            595                 600                 605

Gln Gln Gln Thr Glu Ala Asp Gly Glu His Gly Gln Gly Arg Tyr Pro
            610                 615                 620

Ser Ala Glu Gly Ser Thr Ser Pro Thr Leu Met Glu Gly Arg Met Ala
625                 630                 635                 640

Ile Val Ser Asp Tyr Asp His Ile Pro Glu Ser Phe Val Arg Pro Ser
                645                 650                 655

Lys Thr Cys Pro Lys Gly Ser Asn Val Gly Thr Gly Tyr Ala Ser Leu
            660                 665                 670

Leu Pro Val Ile Cys Ala Cys Gln Arg Thr Leu Ala Glu Leu Ile Ile
            675                 680                 685

Phe Cys Ser Ile Ser Pro Glu Arg Asn Val Leu Arg Arg Asp Gly Ile
            690                 695                 700

Pro Ile Pro Asn His Gln His Met Leu Val Glu Leu Cys Val His Arg
705                 710                 715                 720

Leu Val Ile Asp Val Ile Leu Ala Pro Phe Ser Lys Phe Gly Val Arg
                725                 730                 735

Ala Asp Arg Ser Val Gly Lys His Ala Gln Cys Cys Gly Gln Trp Gly
            740                 745                 750

Cys Ser Ser Trp Leu Pro Pro Leu Pro Leu Ser Gly Gly Val Val Asp
            755                 760                 765

Val Asn Asp Leu Leu Leu Lys Met His Arg Glu Ile His Ile Val Cys
770                 775                 780

Arg Leu Gly Phe Arg Leu Leu Arg Gln Met Val Arg Gln Ala Pro Glu
785                 790                 795                 800

Leu Lys Ala Gly Phe Glu Asn Tyr Ile Pro Tyr Phe Leu Ala Phe Asp
                805                 810                 815

Gly Tyr Lys Leu Glu Val Val Asp Ser Leu Thr Arg Leu Phe Ser Glu
            820                 825                 830

Asn Pro Ala Val Arg Asn Ser Ser Leu Glu Leu Val Val Asn His Tyr
            835                 840                 845

Ile Ala Gly Leu His Leu Thr Arg Ser Gly Arg Tyr Leu Gln Leu Leu
850                 855                 860

Cys Ser Met Cys Ser Val Gly Thr His Gly Val Thr Glu Arg Gln Arg
865                 870                 875                 880

Leu Val Cys Gln Lys Leu Leu Val Glu Asn Ala Asn Ala Leu Tyr Ser
                885                 890                 895

Phe Val Leu Asp Ser Gly Gly Glu Trp Ala Val Lys Thr Asp Lys Asp
            900                 905                 910

Glu Pro Pro Ile Pro Cys Asn Ile Leu Phe Ser Gly Gln Gln Gln Asp
            915                 920                 925

Gly Gly Glu Glu Glu Gly Thr Lys Leu Arg Glu Tyr Val Gln Ser Glu
930                 935                 940

Leu Glu Leu Leu Gly Ala Leu Cys Leu Asp Gly Cys Pro Pro Leu Cys
945                 950                 955                 960

Arg Glu Glu Val Ala Lys Val Phe Pro Ser Pro Val Leu Leu Arg Ala
                965                 970                 975

Leu Arg Asn Phe Ser Pro Lys Trp Pro Glu Val Ser Arg Ser Arg
            980                 985                 990
```

-continued

```
Val Cys Asp Val Val Arg Ser His Leu Ile Arg Leu Ala Met His Cys
            995                 1000                1005

Tyr Ile Leu Pro Tyr Ile Asp Pro Ala Val Gln Leu Arg Glu
       1010                1015                1020

Gly Ala Val Leu Leu Gly Ser Ser Lys Leu His Leu Lys Val Asp
       1025                1030                1035

Glu Lys Thr Ala Phe Ser Gly Lys Pro Asp Ser Glu Leu Thr Gln
       1040                1045                1050

Ala Val Lys Glu Gly Thr Leu His Val Ile Arg Ser Asn Thr His
       1055                1060                1065

Phe Val Arg Ser Asp Thr Gly Arg Ser Ile Leu Ile Arg Ala Ala
       1070                1075                1080

Leu Ala Ala Trp Leu Arg Phe Val Ser Ala His Gln Val Ser Ala
       1085                1090                1095

Thr Glu Thr Ala Cys Leu Val Pro Leu Leu Glu Leu Leu Asp
       1100                1105                1110

Ser Arg Asp Asp Glu Ala His Asp Gly Ser Ser Lys Ile Ala Glu
       1115                1120                1125

Tyr Thr Trp Thr Arg Leu Glu Val Ser Glu Ala Gly Leu Leu Val
       1130                1135                1140

Val Arg Ala Arg Glu Met Ile Cys Gln Ile Leu Leu Gln Ile Leu
       1145                1150                1155

Glu Thr Ala Thr Tyr Arg Ala Ala Asn Glu Ile Asn Leu Leu Leu
       1160                1165                1170

His Gly Ile Leu Val Thr Asp His Gly Ala Ser Leu Ala His Gln
       1175                1180                1185

His Asp Tyr Cys Ser Leu Leu Arg Arg Ala Asp Val Ser Ser Thr
       1190                1195                1200

Gly Asp Pro Phe Val Thr Ser Pro Thr Glu Arg Asp Ala Leu Leu
       1205                1210                1215

Trp His Lys Gly Lys Ala Asn Asp Gly Asn Gly Asn Arg Cys Phe
       1220                1225                1230

Gly Leu Asn Arg Arg Lys Gly Pro Ser Asp Tyr Gln Ser Thr Val
       1235                1240                1245

Ala Gly Ser Ala Val Thr Thr Gln Leu Ser Gly Ser Thr Lys Asp
       1250                1255                1260

Val Ala Ala Phe Leu Asp Tyr Val Lys Gly Ile Cys Ser Cys Ile
       1265                1270                1275

Val Arg Pro Leu Arg Val Asp Gln Leu Val Pro Arg Leu Val Asp
       1280                1285                1290

Leu Ala His His Asp Gly Ser Gln Leu Ala Pro Tyr Ala Met Glu
       1295                1300                1305

Leu Leu Val Arg Ile Cys Thr Val Arg Arg Ser Val Ala Arg Leu
       1310                1315                1320

Val Leu Gln Val His Pro Phe Pro Ser Ser Glu Val Ile Gln Cys
       1325                1330                1335

Phe Asp Asn Met Tyr Phe Ala Ala Val Gln Val Arg Ser Ser Tyr
       1340                1345                1350

Ile Arg Gly Ser Val Glu Glu Ala Ile Asp Val Ala Leu Gln Gly
       1355                1360                1365

Ile Asp Gly Leu Ser Thr Gln Thr Gln Asn Glu Val Thr Gly Thr
       1370                1375                1380
```

-continued

Thr Asn Glu Gly Arg Val Asp Asp Gly Gly Thr Asp Glu Tyr Tyr
    1385                1390                1395

Asn Asp Leu Thr Glu Asp Asp Glu Glu Ile Glu Glu Ile Gly Ile
    1400                1405                1410

Cys Glu Glu Gln Glu Val Glu Ala Ser Ser Ser Ala Pro Glu
    1415                1420                1425

Asp Gln His Glu Val Gly Gly Glu Asn Lys Ala Arg Arg Leu Trp
    1430                1435                1440

Leu Lys Ala Ala Gly Ala Ala Arg Ile Val Val Tyr Arg Asn Ala
    1445                1450                1455

Ile Ile Ala Arg Arg Arg Ser Val Gly Leu Ser Glu Thr Ser Arg
    1460                1465                1470

Val Pro Leu Arg Val Val Arg Ala Glu Thr Val Arg His Trp
    1475                1480                1485

Gln Val His Ile Thr Met Leu Glu Met Tyr Pro Phe Ile Gly Pro
    1490                1495                1500

Ser Ser Pro Ala Phe Ser Lys Trp Met Arg Phe Phe Tyr Val Phe
    1505                1510                1515

Thr Leu Ser Gln Ser Asn Ala Glu Ser Leu Lys Ala Tyr Ile Asp
    1520                1525                1530

Val Phe Met Gly Ala Phe Asn Leu Ser Ser Asn Cys Val Val Met
    1535                1540                1545

Gly Leu His Ile Val Leu Ser Ile Leu Ala Thr Ile Lys Asp Pro
    1550                1555                1560

Thr Pro His Leu Thr Asp Ala Phe Leu Arg Glu Ser Ala Arg Tyr
    1565                1570                1575

Ile Asp Gly Glu Ile Ala Ala Leu His Pro Asp Gly Glu Phe Ala
    1580                1585                1590

Thr Lys Leu Gly Leu His Val Phe Thr Lys Thr Thr Val Gly Gly
    1595                1600                1605

Ile Pro Arg Arg Arg Met Leu Gln Leu Leu Arg Asp Tyr Asp Ala
    1610                1615                1620

Phe Arg Cys Leu Pro Ser Pro Gly Val Thr Glu Lys His Gly Arg
    1625                1630                1635

Gly Arg Phe Thr Ala Cys Ile Val Glu Met Val Cys Arg Ile Cys
    1640                1645                1650

Gly Thr Ser Met Gly Ala Val Ala Leu Gly Arg Ser Ala Leu Pro
    1655                1660                1665

Val Thr His Leu Leu Glu Ile Thr Leu Ser Tyr Gly Thr Ser Tyr
    1670                1675                1680

Thr Pro Leu Val Glu Val Pro Arg Pro Arg Ala Leu Trp Glu Ser
    1685                1690                1695

Asn Ser Phe His Leu Leu Gly Ala Tyr Leu Leu Ala Leu Val Ser
    1700                1705                1710

Leu Tyr Ile Ala Ala Gly Asp Ala Gly Asp Gly Gly Arg Arg
    1715                1720                1725

Gln Arg Gln Met Glu Trp Met Ala Asn Arg Asp Trp Trp Ser Val
    1730                1735                1740

Val Leu Leu Leu Ser Arg Gln Leu Lys Glu Leu Thr Arg Leu Met
    1745                1750                1755

Gln Ser Arg Thr Glu Thr Val Leu Trp Arg Gly Arg Arg Ile Leu
    1760                1765                1770

Gln Arg Tyr Arg Arg Leu Trp Leu Val Asn Leu Pro Leu Ala Leu

-continued

```
           1775                1780               1785

Leu Thr Phe Met Thr Glu Cys Phe Asn Glu Ala Gly Phe Tyr Arg
           1790                1795               1800

Tyr Arg Asp Val Val Gly Ala Thr Phe His Glu Met Cys Met Ser
    1805                1810               1815

Val Ala Gly Phe Ser Glu Val Leu Leu Ala Ser Ala Asp Ala Ile
    1820                1825               1830

Arg Leu Gln Ala Arg Glu Met Val Gly Tyr Arg Arg Leu Val Ala
    1835                1840               1845

Leu Leu Gln Val Gln Thr Gly Asn Leu Val Gly His Glu Leu Leu
    1850                1855               1860

Ser Gly Thr Met Leu Thr Thr Arg Arg Asn Leu Arg His Gly Val
    1865                1870               1875

Ile Cys Tyr Tyr Lys Lys Ile Asn Glu Ala Glu Glu Ala Arg
    1880                1885               1890

Gly Leu His Pro Asp Ala Leu Pro Leu Ala Glu Thr Gly Pro Gln
    1895                1900               1905

Ala Glu Asn Asp Gly Ile Gln Gly Gly Leu Ile Ala Thr Ala Asp
    1910                1915               1920

Val Pro Thr His Thr Gln Asn Asp Ala Asp Ser Ser Pro Met
    1925                1930               1935

Gly Leu Leu Ile Ser Gly Ala Ala Thr Lys Cys Leu Asp Ala Glu
    1940                1945               1950

Arg Leu Arg Gly Ala Leu Arg Ser Leu Val Asn Arg Asp Gln Leu
    1955                1960               1965

Ile Thr Met Glu Asp Ser Thr Asp Leu Gly Glu Pro Ala Gly Ile
    1970                1975               1980

Met Asn Ala Leu Leu Leu Ser Cys Arg Glu Arg Ser Asn Val Leu
    1985                1990               1995

Asp Phe Val Ser Thr Thr Leu Gly Cys Met Arg Glu Arg Ser Phe
    2000                2005               2010

Gly Ser Ile Thr Leu Ile Gly Met Leu Asn Ile Phe Ser Asn Ala
    2015                2020               2025

Leu His Thr Ala Leu Arg Glu Gln Glu Arg Glu Arg Leu Lys His
    2030                2035               2040

Val Ser Ala Glu Asn Ser Ser Val Ile Thr Asp Ile Phe Thr Val
    2045                2050               2055

Arg Ser Phe Glu Thr Asp Tyr Ala Lys Glu Asn Ala Gly Arg Leu
    2060                2065               2070

Leu Gln Thr Thr Phe Ser Asp Leu Gly Ala Thr Arg Ala Ile Ala
    2075                2080               2085

Ser Leu Cys Ala Val Asp Asp Gln Val Val Ala Tyr Ser Ala Val
    2090                2095               2100

Gln Leu Cys Val Gly Leu Leu Glu Gly Gly Asn Glu His Ala Gln
    2105                2110               2115

Lys Ala Leu Leu Ala Tyr Phe Gln Glu His Gln Glu Arg Phe Phe
    2120                2125               2130

His Asn Ile Arg Asp Met Leu His Lys Ala Val Asp Trp Val Gln
    2135                2140               2145

Cys Thr Asn Ala Glu His Gln Ile Val Val Leu Glu Arg Gly Gly
    2150                2155               2160

Val Val Pro Asn Val Ser Asn Ala His Glu Phe Thr Arg Met Leu
    2165                2170               2175
```

-continued

Leu Thr Asn Ala Leu Thr Thr Pro Pro Ser Leu Tyr Ser Ser Leu
2180            2185                2190

Lys Val Arg Val Gly Arg Gly Ala Ala Val Ala Arg Arg Arg Leu
2195            2200                2205

Ser Ala Trp Asp Arg Ala Gly Gly Ser Leu Asn Gln Arg Phe Val
2210            2215                2220

Cys Thr Leu Phe Arg Met Leu Gln Leu Phe Cys Glu Gly His Asn
2225            2230                2235

Leu Ser Met Gln Asn Tyr Ile Arg Ser Gln Tyr Asp Asn Leu His
2240            2245                2250

Ser Val Asn Ala Val His Glu Val Met Asn Leu Ile Thr Glu Ile
2255            2260                2265

Ala Ala Val Val His Pro Ala Thr Val Arg Met Leu Gln Ser Ala
2270            2275                2280

Phe Ala Leu Leu Thr Glu Leu Cys Gln Gly Pro Cys His Glu Asn
2285            2290                2295

Gln Glu Ala Leu Leu Gly Tyr Gly Val Cys Val Ile Ile Ser Lys
2300            2305                2310

Leu Leu Ser Arg Leu Asn Leu Pro Asp Val Thr Gly Thr Pro Ser
2315            2320                2325

Thr Gly Thr Gly Ile Thr Asn Trp Gly Gly Gly Asp Ser Asn Ser
2330            2335                2340

Thr Asp Asn Lys Ala Ser Val Asp Cys Cys Thr Leu Asn Glu Thr
2345            2350                2355

Asp Ser Glu Gly Asn Ala Phe Leu Arg Leu Gln Gly Gly Phe Leu
2360            2365                2370

Leu Ser Lys Asp Asp Ala Gly Asn Leu Arg Ile Ala Leu Thr Gln
2375            2380                2385

Cys Leu Leu Ser Leu Ile Glu Gly Cys Arg Ser Arg Asp Val Phe
2390            2395                2400

Arg Gln Leu Leu Glu Gln Ile Pro Val Glu Val Ile Glu Arg Glu
2405            2410                2415

Leu Thr Thr Val Asp Pro Gly Ala Tyr Asp Ser Ile Leu Glu Asn
2420            2425                2430

Glu Glu Leu Ala Ser Asp Pro Gly Val Glu Ala Leu Phe Asn Trp
2435            2440                2445

Leu Ile Phe Leu Lys Thr Val Arg Pro Tyr Ala Glu Ala Asp Tyr
2450            2455                2460

Leu Lys Arg Ile Asp Ala Met Leu Gln His Thr Asn Lys Leu Cys
2465            2470                2475

Thr Arg Leu Gly Phe Ile Glu Ile Gln Arg Ala Asp Gly Met Leu
2480            2485                2490

Glu Lys Val Leu Phe His Ile Pro His Val Trp Arg Gly Leu Met
2495            2500                2505

Arg Arg Asn Arg Lys Gln Met Leu Ala Gly Ile Asn Cys Ser Ser
2510            2515                2520

Arg Ala Ala Lys Leu Gly Asp Phe Met Tyr His Ser Asp Asn Val
2525            2530                2535

Ile Phe Glu Val Glu Arg Ser Tyr Ala Phe Gln Cys Trp Val Glu
2540            2545                2550

Arg Arg Thr Arg Trp Arg Leu Asp Asn Arg Ser Ser Gly Trp Arg
2555            2560                2565

```
Gly Lys Glu Cys Asp Ala Gly Lys Val Asp Thr Ser Val Asp Ala
2570                2575                2580

Gly Lys Pro Arg Trp Thr Pro Lys Trp Lys Gln Cys Ser Asp Ala
2585                2590                2595

Pro Lys Tyr Phe Trp Asn His Phe Ile Ala Pro Val Leu Phe Cys
2600                2605                2610

Thr His Leu Gly Phe Tyr Glu Tyr Ser Ser Leu Leu Val Ala Val
2615                2620                2625

Val Leu Asn Ile Ala Leu Ile Asn Gly Glu Gly Arg His Arg Asn
2630                2635                2640

Leu Glu Glu Ser Gln Leu Trp Ala Asn Ile Ile Ser Gly Leu Cys
2645                2650                2655

Val Leu Gln Leu Val Leu Ser Leu Ile Ala Ile Thr Val Asp Thr
2660                2665                2670

Ile Val Phe Phe Pro Val Ser Leu Tyr Val His Tyr Arg Gln Lys
2675                2680                2685

Gln Gln Arg Phe Ser Gly Arg Ala Lys Phe Asn Glu Thr Leu Gln
2690                2695                2700

Gly Val Leu Arg Gly Leu Ser Ala Lys Glu Ile Ser Leu Leu Leu
2705                2710                2715

Val Thr Arg Phe Ser Phe Gln Tyr Arg Leu Leu Leu Val Val Met
2720                2725                2730

Ala Val Leu Ser Ile Phe Val Ser Tyr Tyr Phe Ala Ala Ala His
2735                2740                2745

Leu Thr Leu Met Val Tyr Thr Phe Pro Thr Leu Arg Thr Phe Val
2750                2755                2760

Ser Ala Ile Thr His Asn Gly Arg Gln Leu Leu Leu Thr Ala Leu
2765                2770                2775

Leu Gly Val Met Gly Leu Tyr Leu Phe Ala Ile Ala Gly Arg Ile
2780                2785                2790

Met Phe Pro Glu Gln Phe Gly Ser Asn Gly Glu Val Asp Glu Asn
2795                2800                2805

Ser Gly Lys Lys Asn Asp Glu Asn Gly Asn Cys Asp Thr Leu Leu
2810                2815                2820

Arg Cys Phe Thr Phe Ile Leu Trp Gln Gly Leu Arg Gln Gly Gly
2825                2830                2835

Gly Val Gly Asp Val Met Asp Glu Val Ser Trp Asn Ser Ser Thr
2840                2845                2850

Leu Val Pro Arg Val Ser Tyr Asp Leu Ile Phe Phe Ala Leu Val
2855                2860                2865

Asn Val Val Phe Leu Asn Ile Met Phe Gly Ile Ile Ile Asp Thr
2870                2875                2880

Phe Gly Glu Leu Arg Asp Asp Arg Arg Glu Arg Glu Asn Asp Leu
2885                2890                2895

Arg Ser Thr Cys Phe Ile Cys Gly Leu Asp Ala Asp Thr Leu Glu
2900                2905                2910

Lys Gly Gln Val Gly Gly Phe Arg Ala His Val Glu Asp Ala His
2915                2920                2925

Asn Met Trp Met Tyr Leu Tyr Phe Ile His Tyr Leu Arg His Lys
2930                2935                2940

Asp Pro Asn Glu Phe Thr Gly Gln Glu Ser Tyr Val His Glu Lys
2945                2950                2955

Ile Gln Arg Asn Asp Leu Ser Phe Phe Pro Glu Glu Asp Cys Leu
```

```
                    2960                2965                2970
Ala Leu Gln Glu Cys Arg Glu Gly Asn Gly Lys Arg Thr Gly Asp
        2975                2980                2985

Asp Glu Ala Asp Ser Asp Asp Glu Leu Ala Ser Ser Val Val Val
        2990                2995                3000

Gly Gly Ser Ala Pro Arg Gly Pro Lys Pro Glu Ser Ala His Pro
        3005                3010                3015

Asp Thr Gly Val Lys Leu Val Leu Lys Glu Leu Ala Ala Val Arg
        3020                3025                3030

Glu Ala Val Ser Ala Leu Ala Arg Glu Ala Thr Met Glu Gly Glu
        3035                3040                3045

Arg Thr Arg Gly Leu Ala Gln Gln Leu Glu Leu Ile Asn Arg Ser
        3050                3055                3060

Ser Gln Ser Ser Ser Leu Arg Lys Phe Pro Gly Gly Gly Ser Ala
        3065                3070                3075

Ala Ser Val Ala Glu Thr Ser Thr Ser Lys Gly Thr Trp Leu Arg
        3080                3085                3090

His Ser Glu Pro Glu His
        3095

<210> SEQ ID NO 12
<211> LENGTH: 9300
<212> TYPE: DNA
<213> ORGANISM: Trypanosoma brucei

<400> SEQUENCE: 12
atgagccaaa gccgtgttcc tataaggtat ggagccttta ttcacctctc ctgcgacgaa      60
gggtacgtta cagcgggagg gttgggtaat gaagggttgt tcatacggaa caagaatgag     120
ctaagcgacg atgccgagcc actaccgctt tttgggtttg aaacaagcgt ttttcagatc     180
ctacctccaa cagtggctaa agtcgcggca gaggaggggt tgagcaaagg caaccgggct     240
ccaaacagca accctctttc ggacggtgtc agtaatattt actcgacaca acaggtgact     300
ttcgggcaat tgtttgtgct ggtccatgcg gtgagccgcc tacacgtggc ggcactgccg     360
tcggaacctt ctgagaggga ccctgactgc gcccggcttg tgctcgcacc gcctggtgaa     420
attgagcaaa ccttctgcca gtttatcttc acaccgcgtt acacaacgca cggtgaagga     480
gatgtcgtgt gccgaggtga tgaagtattg gtgcagctgt ccagcatccc tatattcctt     540
caaactacgg tggtgtcacc tacacgcccg gtaaaacacg aaacttttgg aagtgcaagc     600
ttcccctacg aaccgactga tggatgtgga cgtgggaaca gttggagtgc tggcaccccgt    660 atggcactat ctgctgtgtt gggagcacca gaggttaact tatcggaggc aaaagcactc     720 gttttgttg ttgagcgcta tgacatcgat cgagataaag cggaacatca acgtattctg      780
caccgcatcc cccggccgtg cgtttccgca ggtgtgccgg taatattta ccatctcgag      840 cacaagcggg tactggctac gagtgtcgca atgcccccctt gccaaggggg tgcaagatt     900 ggagtgtcag gcgtggcgcc aagggcaat gaaggtggtg gggaacgcga tcatttgctc      960
aagacaagac agactcactc agtgatggga aatgttaccg tgatatgcca cgcttcaggg    1020
aggtttgctg cggcggggag ttcgaagtcg cagggaagtg attcccattc cgcaggagcg    1080
acaagcctcg actccgaccc atgtagcact aaaggaaagg caccccgatga ccgtaaaagg   1140 gtgaatggtg tcgtggtgc cgccctcccg ctcttcgcag tggataaggg tgtagctgat     1200
ggaacgttca gtgaagaggg agccctcagc gggttgcagt gcagttgcac cgctttgtgg    1260
```

```
atattagaaa acgagcaacc aacggtaggt ggggccgtga atatgaattc gggagtgtat    1320
cgcctccgtc aagcctgttc taacttatac gttgctgtgg aagggtcagc cgttgatact    1380
atacttgagg gggacggttc tcctgaggga tctgttgtgt cgcagaggtc ctgttgtaac    1440
ctcactggag atatcgtaaa cgaggagggg ggtgatgtgg ttcgccccac aacgctgtcc    1500
atgattccgc caccacgtac accgaaagac cttcaacgca cacttttcag actaagcccc    1560
atgtttaaca cagattgcgg gtatcttatc gagaatgact gcttgctact gcagaacgtc    1620
gccacagaca tgtatctgtg cacaagtgag ggaagtgaaa ctctttctct atcatggaag    1680
ccatcaaata ttgatttgat agtcgtccga agggccgcaa cggacgtcca ggatagcgtc    1740
ctatttcttt ggtcccaatg tgaaacactt agtgggtacc gtgatgcctt ccaggtactg    1800
acaacggaag gaacggcaac gcaccagcaa caaacgaaaa cggacggtga acatggacag    1860
ggcaggtatc cttcggcaga aggctcaacc agccccactc tgatggaagg aagaatggca    1920
attgtatcgg attataatca cattccagaa agttttgtac gacctagcaa aacgtgcccc    1980
aaaggcagta acgtaggtac tggttatgct tcgcttcttc cggttatttg tgcctgccag    2040
cgtacactcg cccgagctcat aattttttgt tcaatctctc ctgaacgaaa tgttctgcga    2100
agagacggca tacctatccc gaaccaccag catatgttgg ttgaactgtg cgttcaccgc    2160
ctagttattg atgttattct cgcccccttt tcaaagtttg gggtgagagc tgaccgatcg    2220
gtgggaaagc atgcacaatg ctgcgggcag tgggctgtt cttcttggct ccaccgctt    2280 ccactgtctg gcggagtggt ggatgttaac gaccttttac tgaagatgca ccgagagatt    2340
catatcgtct gtcgtcttgg ttttcgactc ttaaggcaaa tggtccgtca agcgccggag    2400
ctcaaggcag ggtttgaaaa ctatataccg tattttctgg cttttgacgg gtacaagcta    2460
gaggttgtcg attcgctgac aaggctcttt tcggagaacc ccgccgtgag gaactcatct    2520
ttggaacttg tggttaatca ctacatcgct ggcctccacc tcacgcgttc cggaagatat    2580
ctgcagttgc tatgctccat gtgttctgtt gggacccacg gcgtgacgga acgtcagcga    2640
cttgtgtgtc aaaaacttct cgttgaaaat gctaacgcat tgtacagctt tgtgcttgat    2700
agtggcggcg agtgggccgt taaaactgac aaggatgaac cgccaatacc gtgtaacatc    2760
cttttttcag gacagcaaca agcggcgga gaagaggaag gaacgaagct gagggaatac    2820
gtgcagagcg aattggagct actgggtgcc ctgtgtctgg atgggtgccc acctttatgt    2880
agggaagaag tagccaaagt gttcccttca ccagtgctcc tgatggcttt acgcaacttt    2940
tcgccgaaat ggcctgaagt gagcgaccgg tcgcgcgtct gtgacgttgt gcggagtcat    3000
ttaatacgtc tcgcaatgca ctgctacatc cttccatata tcgatgaccc agctgtgcag    3060
ctacgcgagg gcgccgtcct gctaggttcc agcaagttgc atctcaaagt cgatgaaaaa    3120
acagccttct ctggcaagcc ggacagtgaa ctcacccagg ctgtgaaaga gggaacactc    3180
cacgtcatcc gttctaacac ccattttgta cggtctgaca caggccgtag tatattgatt    3240
cgtgccgcat tagcggcatg gctgcggttc gttagtgcac atcaggtttc cgccacggag    3300
acagcctgtc tggtaccgtt gcttctagag cttcttgata gtagagacga cgaggctcac    3360
gacggcagca gcaaaatagc ggaatacaca tggacacgcc ttgaagtatc cgaagcggga    3420
ctgctcgttg ttcgggctcg agagatgatt tgtcagatcc ttctgcaaat tcttgagacc    3480
gctacttacc gcgcagcaaa tgaaattaac ctactgctgc atggtatttt ggttactgac    3540 cacgcgcca gcctcgccca ccagcacgat tattgttcgt tactccgcag gcggacgtc    3600 tcttcgaccg gagacccgtt tgtcacatcc ccaaccgaaa gagacgcact gctgtggcac    3660
```

```
aaaggcaagg ccaatgacgg taatggaaac cgttgctttg gattgaacag acgcaagggg    3720
cccagcgact accagtcgac ggtagccggt agcgccgtga ccacgcagct cagtggctcc    3780
acaaaggatg ttgccgcctt cttagattac gtcaaaggca tctgcagttg catcgtgcgc    3840
ccactccgtg ttgatcagct ggtaccacgg ctcgtcgatc ttgcacacca cgatggatca    3900
caattggcac catacgccat ggagttgctc gttcgaatct gcacggtgag gcgcagtgtg    3960
gcccgtctcg tgcttcaagt gcatcctttc ccctcctccg aagtgattca atgttttgac    4020
aatatgtatt ttgctgctgt tcaagtgcgg tcatcatata ttcgaggatc cgtggaggag    4080
gccattgatg ttgccctcca gggcatcgac gggttaagca ctcaaactca aaacgaggtg    4140
acaggcacaa cgaatgaggg tagagtggat gacggaggca ccgacgagta ctataatgat    4200
ttaacgaggg atgacgagga gatcgaagaa ataggtattt gtgaagaaca agaagttgag    4260
gcaagctctt cgtcagcccc cgaagaccaa catgaggtcg gaggggaaag caaagcacgg    4320
cgcctgtggt caaaggcagc tggtgcggcc cgcatcgttg tgtatcgaaa cgccataatt    4380
gcacgccgac gttctgttgg actaagcgaa acgtcgcgcg tcccgcttcg cgttgttgtc    4440
cgtgcggaga cagtacgcca ttggcaagtg cacataacta tgctcgaaat gtacccgttc    4500
atcggcccgt cgagccctgc gttcagcaag tggatgcgtt tcttttatgt tttcacgtta    4560
tcccaaagta atgccgagtc gctgaaggcc tacattgata tatttatggg ggccttcaac    4620
cttagcagca actgcgttgt tatgggcctc catattgtcc tcagtattct cgcgacaatc    4680
aaagatccaa caccacacct aactgacgca tttctccgcg agtccgcccg ttacattgat    4740
ggagaaattg ctgctcttca ccccgacgga gagtttgcca ccaagttggg tctccacgtc    4800
ttcaccaaga ccacggttgg gggcattccg cgacgtcgta tgttacagct gttgcgtgac    4860
tatgatgcct tccgctgcct cccctcaccc ggagtgaccg agaagcacgg gcggggtcgc    4920
ttcacagctt gcatcgttga gatggtttgc cgcatttgcg gtacatcaat gggtgccgtg    4980
gcgctggggc ggtcggctct gccagtgact catctcttag aaatcacgct gagctatggc    5040
acatcctaca cccccctggt agaggtgccg cggccccgtg cattgtggga aagtaactcg    5100
ttccatcttc tcggtgctta tctgttggcg ctcgtgtcgc tctacattgc cgcgggcgac    5160
gcagggggag acggggggtcg aagacaacgg cagatggaat ggatggcgaa ccgtgactgg    5220
tggtcggttg tgcttttgct ttcacggcag ctaaaagagc tcacacggct aatgcagtct    5280
agaacagaga ctgtgctatg gcgggacgc cgcattctgc agcggtatcg ccggttgtgg    5340
cttgtcaatt taccgctggc actgttaact ttcatgacag aatgttttaa tgaggcaggt    5400
ttttacaggt accgggacgt tgtgggagct accttccacg aaatgtgtat gagtgtcgcc    5460
gggtttagcg aagtgctcct cgcaagtgct gatgcgatac ggctgcaggc aagagagatg    5520
gtgggttacc gccgcctcgt ggcccttctc caggtccaga cgggaaacct cgtgggtcac    5580
gagcttcttt caggcacgat gttgacgacg cgacgcaatc tacgacacgg cgttatctgc    5640
tactataaga aaataaatga ggccgaagaa gaggcccgcg gactacaccc ggacgctctc    5700
ctgttggccg agaccggacc ccaggctgaa aacgacggca tccagggtgg tttaattgca    5760
acagcggatg tacccacgca cacacaaaac gatgcagaca ctcgtccccc tatgggatta    5820
ctaatatctg gtgctgcgac gaaatgtctt gatgcggagc gactccgtgg tgcactgcgc    5880
agtcttgtga accgtgacca actgatcacc atggaggaca gcacggacct aggtgagccg    5940
gctgggatca tgaacgccct tttgttaagc tgtcgagaac ggtcaaatgt tctagacttt    6000
```

-continued

```
gtgtccacga ctctcggctg catgcgggag cgatcctttg gttccatcac ccttattggt    6060
atgctaaaca ttttctccaa tgcgctacat acagcactca gagaacagga gagagaaaga    6120
ctgaaacatg ttagtgctga gaactcgtcg gtgatcaccg acatttttac ggtgaggagt    6180
tttgaaaccg actatgcaaa ggagaatgcg ggaaggctac tgcagacgac gttcagtgat    6240
ctcggtgcaa cgcgcgctat tgcgtccctc tgcgcagtgg acgaccaggt agtggcctac    6300
agtgctgtac aactctgtgt tggtctcctc gagggtggta atgagcatgc ccagaaagcc    6360
cttctcgcat atttccaaga gcaccaagag agattctttc acaacattcg agacatgctt    6420
cacaaagccg tggattgggt gcagtgtacc aacgcagaac accagatcgt tgtgcttgag    6480
aggggtggag tggttcctaa cgtatccaac gcacacgaat tcacccgcat gcttctgaca    6540
aacgcactca ccacgccccc atcgctctac agcagtctaa agtgagggt cggacgcgt     6600 acagcggttg caagaagacg actttccgcg tgggaccgag caggcggaag tctcaaccaa    6660
cgtttcgttt gcaccctatt tcgtatgctc cagctcttct gtgaagggca caacctcagt    6720
atgcagaact acatccgctc gcagtacgat aatttgcata gcgtaaatgc tgtgcatgaa    6780
gtaatgaacc tcattacgga aatagccgct gttgtccacc cggccaccgt ccggatgctt    6840
cagagtgcat tcgcgctcct aactgagctg tgccaagggc catgtcatga aaatcaagag    6900
gccctgctgg gttacggtgt gtgtgtcgtt atcagcaagt tgctcagccg cctgaatttg    6960
ccggacgtga cgggcactcc atccactgga acaggcatta caaactgggg cggcggtgac    7020
agcaacagta ctgataacaa ggcttcggtc gactgctgca ccctgaatga aacagatagc    7080
gaaggcaacg cttttttacg tctacaaggc ggctttttac taagcaagga cgatgctgga    7140
aacctccgta ttgcactcac acaatgccta ctctcgctta tcgagggatg tcgttcacgg    7200
gacgtattcc accaactgct ggaacagatt ccagtcgaag ttatcgagcg cgagctaacc    7260
acggtggacc caggggcgta cgacagcatt cttgaaaatg aggaactggc gagtgacccg    7320
ggtgtggagg ccctcttcaa ctggcttatt ttcctgaaga ctgtcagacc gtacgcggag    7380
gccgattact tgaaacggat tgatgcaatg cttcagcaca caaataaact atgcactcgc    7440
ctcggattca ttgaaataca acgtgcggat ggaatgctgg agaaagtgct gttccgcatt    7500
ccacacgtct ggcgcgggtt gatgcgtagg aataggaagc agatgctggc ggaaattaac    7560
tgcagcagtc gtgcagcgaa gctcggagac tttatgtacc acagtgacaa cgtgatcttt    7620
gaagtggaac gtagctatgc attccagtgc tgggtagagc gccgcacacg ctggaggttg    7680
gacaacagaa gtagcggttg gagaggtaaa gagtgtgatg ccggcaaagt cgatacttca    7740
gtcgacgcag gcaaacctag gtggacccca aaatggaaac aatgctcaga tgcgcccaaa    7800
tatttctgga accatttcat tgcacccgta ctgttttgca cacacctcgg ttttttacgag   7860 tacagctccc tcctcgtcgc tgtggttttg aacattgctt tgatcaacgg cgaggggcgt    7920
catcggaatc tggaagaatc ccagctctgg gctaacatca tatctggcct gtgtgtcctg    7980
cagcttgtgt tgtctttaat tgcaataact gtggatacta ttgtctttt cccggtgtcg     8040 ctgtacgtac actaccgcca gaaacagcag cggttttccg ggcgggcgaa gttcaacgaa    8100
acattgcaag gggttttacg tgggttgagt gcgaaagaaa tcagtttact gcttgtgacg    8160
cgcttcagtt tccaatatcg cttacttttg gttgtcatgg cggtttttaag catcttcgtt    8220 tcatattact ttgctgccgc acaccttacg cttatggttt acacgtttcc cacacttcgt    8280
acctttgtta gcgccatcac gcacaatggc cgacagttac tcctaacggc cctgcttggt    8340
gtcatgggat tgtatctttt tgccatcgcg ggccgcatta tgttccctga gcaattcgga    8400
```

```
agcaacggtg aggtcgacga aaactcgggg aagaaaaacg acgaaaatgg aaactgcgac    8460
acattgctgc gctgttttac atttattctg tggcaggggc tgcggcaggg tggtggcgtc    8520
ggggatgtca tggatgaggt atcatggaat agctcaacac ttgtaccacg ggtgagctac    8580
gatctcattt tcttcgctct tgtaaatgtt gtcttcctca acatcatgtt tggtatcata    8640
attgacactt tcggtgagtt gcgcgacgac cgacgagaga gggaaaacga actgaggagc    8700
acctgcttta tctgcggcct agacgcggac acacttgaaa agggccaagt gggcggtttc    8760
agggctcatg tggaagacgc acacaatatg tggatgtacc tttactttat tcactacctc    8820
cgtcataagg acccgaacga gtttactggt caagagtcgt acgtccacga gaagattcaa    8880
aggaatgacc tctccttctt tccggaggaa gactgtcttg cgttacaaga atgcagggag    8940
ggcaacggca agagaactgg agatgacgag gctgatagtg atgacgagct tgcgagcagc    9000
gttgtggtag ggggcagtgc accacgcgga ccaaagcctg agagtgcaca tcccgatacc    9060
ggtgtgaaac ttgtgttgaa ggagctggca gctgtgcgtg aagctgtcag tgcccttgcg    9120
cgggaggcca caatggaagg ggagcggacg aggggactcg cccagcagct agagctcata    9180
aaccgcagca gccagagctc atcactgcgg aagtttcccg gcgggggcag cgcagcatcg    9240
gttgctgaga cgagcacaag caagggggacg tggttgcggc actccgaacc agaacactaa    9300
```

THERAPEUTIC AGENT FOR TREATING *TRYPANOSOMA*-ASSOCIATED DISEASE, METHOD FOR KILLING *TRYPANOSOMA* PARASITES, AND USE THEREOF

CROSS-REFERENCE TO RELATED APPLICATIONS

This Nonprovisional application claims priority under 35 U.S.C. §119 on Patent Application No. 2013-211448 filed in Japan on Oct. 8, 2013, the entire contents of which are hereby incorporated by reference.

TECHNICAL FIELD

The present invention relates to a therapeutic agent for treating a *Trypanosoma*-associated disease, a method of preventing infection by the parasitic protozoa, trypanosomes (*Trypanosoma* parasites), or killing *Trypanosoma* parasites, and use of the therapeutic agent.

BACKGROUND ART

A *Trypanosoma*-associated disease, or trypanosomiasis, is a general term for diseases that develop due to infection by the parasitic protozoan of the genus *Trypanosoma* of the phylum kinetoplastea of the superclass Mastigophora. Every year, many humans and animals such as farm animals are reported to have died from *Trypanosoma*-associated diseases. The damages caused by *Trypanosoma* parasites are tremendous and serious.

Several therapeutic agents for treating a *Trypanosoma*-associated disease have been developed so far. However, those therapeutic agents must be used in early treatment, and also have problems such as production of severe side effects and development of resistant trypanosomes. No vaccine for treating a *Trypanosoma*-associated disease has been developed so far, and no effective therapeutic agent or method has been established as well.

As treatment of a disease, there is known a state-of-the-art treatment which uses an oligonucleotide and works by silencing a gene that responds to the disease. Examples of such a therapeutic method include a treatment which uses RNA interference using dsRNA (Non-patent Literature 1).

However, it has been reported that against *Trypanosoma cruzi*, which is a pathogen of American trypanosomiasis (Chagas disease), RNA interference cannot be achieved since dsRNA is degraded in both epimastigotes which are parasitic in insect vectors and amastigotes which have a proliferative phase in mammalian cells (Non-patent Literature 2).

CITATION LIST

Non-Patent Literatures

Non-Patent Literature 1

Barker R H Jr et al., Proc Natl Acad Sci USA 93:514-518, 1996

Non-Patent Literature 2

DaRocha W D et al., Mol Biochem Parasitol 133:175-86, 2004

SUMMARY OF INVENTION

Technical Problem

As described above, no effective therapeutic method using an oligonucleotide has been reported as a therapeutic method of treating an infectious disease caused by *Trypanosoma* parasites.

The present invention is made in order to solve the problem. An object of the present invention is to provide a therapeutic agent for treating a *Trypanosoma*-associated disease, a method of preventing infection by the parasitic protozoa, trypanosomes (*Trypanosoma* parasites), or killing *Trypanosoma* parasites, and use of the therapeutic agent, each of the therapeutic agent, the method, and the use using a mechanism different from a mechanism used in conventional art.

Solution to Problem

In order to attain the object, the present invention encompasses any one of the following aspects.

(1) A therapeutic agent for treating a *Trypanosoma*-associated disease, including, as a medicinal component, an antisense oligonucleotide suppressing the expression of an inositol 1,4,5-trisphosphate receptor protein of *Trypanosoma* parasites.

(2) The therapeutic agent as set forth in (1), wherein the antisense oligonucleotide is at least one selected from the group consisting of an oligonucleotide including the base sequence of SEQ ID NO: 1, an oligonucleotide including the base sequence of SEQ ID NO: 2, an oligonucleotide including the base sequence of SEQ ID NO: 3, and an oligonucleotide including the base sequence of SEQ ID NO: 4.

(3) The therapeutic agent as set forth in (1) or (2), wherein the antisense oligonucleotide is at least one selected from the group consisting of an oligonucleotide consisting of the base sequence of SEQ ID NO: 1, an oligonucleotide consisting of the base sequence of SEQ ID NO: 2, an oligonucleotide consisting of the base sequence of SEQ ID NO: 3, and an oligonucleotide consisting of the base sequence of SEQ ID NO: 4.

(4) The therapeutic agent as set forth in (1), wherein the antisense oligonucleotide is an oligonucleotide including a base sequence having 90% or more sequence identity with any one of the base sequences of SEQ ID NOs: 1 through 4.

(5) A method of treating a *Trypanosoma*-associated disease, including the step of administering, to a human or an animal, a therapeutically effective amount of the therapeutic agent set forth in any one of (1) through (4).

(6) The method as set forth in (5), wherein a timing of administering the therapeutic agent is determined in accordance with a form of *Trypanosoma* parasites in the human or the animal.

(7) The method as set forth in (5) or (6), wherein the timing of administering the therapeutic agent is determined so that a concentration of the therapeutic agent in blood will be a therapeutically effective amount in a period in which a form of *Trypanosoma* parasites in the human or the animal is a bloodstream form of trypomastigote.

(8) The method as set forth in any one of (5) through (7), wherein the *Trypanosoma* parasites are at least one of *Trypanosoma cruzi*, *Trypanosoma brucei* complex, *Trypanosoma evansi* (*T. evansi*), *Trypanosoma vivax* (*T. vivax*), and *Trypanosoma congolense* (*T. congolense*).

(9) A drug for suppressing the expression of an inositol 1,4,5-trisphosphate receptor protein of *Trypanosoma* parasites, including, as an active component, an antisense oligonucleotide suppressing the expression of the inositol 1,4,5-trisphosphate receptor protein.

(10) A method of preventing infection by *Trypanosoma* parasites, or killing *Trypanosoma* parasites, including the step of supplying an effective amount of the drug set forth in claim 9 to *Trypanosoma* parasites.

(11) A method of preventing secondary infection with a *Trypanosoma*-associated disease, including the step of supplying the drug set forth in (9) to blood which is present outside a body of a human or an animal and is infected or likely to be infected by *Trypanosoma* parasites.

(12) A screening method for screening a candidate for a therapeutic agent for treating a *Trypanosoma*-associated disease, including (i) a first step of adding, in vitro and while *Trypanosoma* parasites are in a trypomastigote form, a drug to be screened and then (ii) a second step of selecting the drug as a candidate for the therapeutic agent in a case where the addition of the drug has caused growth of the *Trypanosoma* parasites to be suppressed, caused infection of the *Trypanosoma* parasites to be prevented, or caused the *Trypanosoma* parasites to be killed.

Advantageous Effects of Invention

The present invention makes it possible to provide a therapeutic agent for treating a *Trypanosoma*-associated disease, a method of preventing infection by *Trypanosoma* parasites, or killing *Trypanosoma* parasites, and use of the therapeutic agent, each of the therapeutic agent, the method, and the use using a mechanism different from a mechanism used in conventional art.

BRIEF DESCRIPTION OF DRAWINGS

FIG. 3 shows results obtained in a case where (i) trypomastigotes over-expressing an EGFP-TcIP$_3$R fusion protein were cultured for various time periods in the presence of an antisense oligonucleotide (SEQ ID NO: 3) or a sense oligonucleotide (SEQ ID NO: 7) and (ii) western blotting was carried out with use of an anti-EGFP antibody or an antitubulin antibody as an internal control.

DESCRIPTION OF EMBODIMENTS

Figure 1:
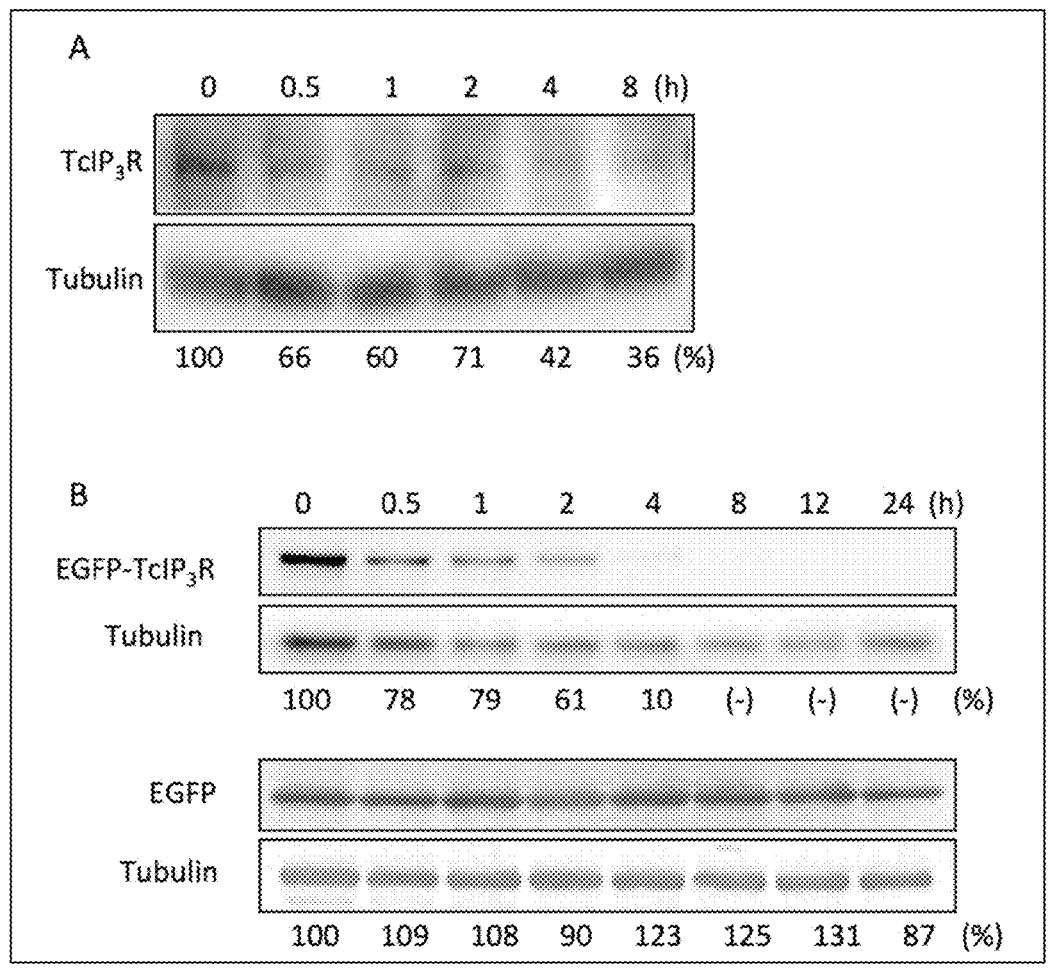
FIG. 1 is a view showing a life span of an inositol 1,4,5-trisphosphate receptor (TcIP$_3$R) protein in epimastigotes of *Trypanosoma cruzi*. A of FIG. 1 shows an expression level of native TcIP$_3$R, and B of FIG. 1 shows an expression level of a recombinant EGFP-TcIP$_3$R fusion protein.
Figure 2:
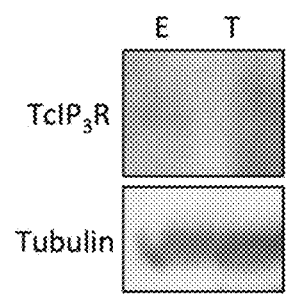
FIG. 2 is a view showing that an expression level of a TcIP$_3$R protein is very low in trypomastigotes.

[1. Therapeutic Agent for Treating *Trypanosoma*-Associated Disease]

In a living organism, a dynamic change in intracellular calcium ion (Ca$^{2+}$) concentration plays an important role in cellular signaling and physiological function. Phosphoinositide-phospholipase C (PI-PLC) is activated in response to an external stimulus via a receptor on a cell surface, and catalyzes hydrolysis of phosphatidyl inositol 4,5-diphosphate (PIP$_2$). This produces D-myoinositol 1,4,5-trisphosphate (IP$_3$) and sn-1,2-diacylglycerol (DAG), which are two important second messengers. IP$_3$ accelerates release of Ca$^{2+}$ from intracellular stores, whereas DAG activates protein kinase C (PKC).

An inositol 1,4,5-trisphosphate receptor (IP$_3$ receptor, hereinafter referred to as IP$_3$R) protein is a Ca$^{2+}$ channel localized in an endoplasmic reticulum (ER). IP$_3$R is activated by binding to IP$_3$, and initiates Ca$^{2+}$ signaling.

The inventors of the present invention revealed that a homologue (TcIP$_3$R) of an IP$_3$R protein in *Trypanosoma cruzi* is an essential protein for *Trypanosoma cruzi* and is involved in the abilities of *Trypanosoma* parasites to (i) undergo division and proliferation, (ii) undergo transformation from one growth phase to another growth phase, and (iii) infect host cells. Further, the inventors of the present invention showed that the TcIP$_3$R protein in vivo serves as a determination factor of toxicity of *Trypanosoma* parasites. Further, a primary structure of the TcIP$_3$R protein has very little homology with a primary structure of a human IP$_3$R protein group. The inventors therefore assumed that the TcIP$_3$R protein is a suitable candidate for a target of a therapeutic agent for a *Trypanosoma*-associated disease. The inventors then tried to suppress the expression of the TcIP$_3$R protein by use of an antisense oligonucleotide, and successfully prevented infection by *Trypanosoma* parasites, by suppressing the expression of the TcIP$_3$R protein in a trypomastigote form of *Trypanosoma* parasites. Further, the inventors newly found that the use of an antisense oligonucleotide makes it possible to provide (i) an extremely effective therapeutic agent for treating a *Trypanosoma*-associated disease and (ii) an extremely effective method of preventing infection by *Trypanosoma* parasites, or killing *Trypanosoma* parasites. On the basis of the finding, the inventors made the present invention.

(Definition of Treatment of *Trypanosoma*-Associated Disease)

The *Trypanosoma*-associated disease to be treated in the present invention is a concept which refers to a broad range of states in which a human or an animal (other than humans, the same also applies to the following descriptions) is infected by the parasitic protozoa, trypanosomes (*Trypanosoma* parasites) of the genus *Trypanosoma*. The concept encompasses not only, as a matter of course, states in which onset of a symptom specific to a *Trypanosoma*-associated disease is observed in a human or an animal, but also states before the onset of the symptom. The *Trypanosoma*-associated disease is a zoonosis, and trypanosomiasis consists of African trypanosomiasis and American trypanosomiasis. Further, African trypanosomiasis and American trypanosomiasis each include human trypanosomiasis which develops in humans and animal trypanosomiasis which develops in animals other than humans. Animal trypanosomiasis includes nagana and sura.

The *Trypanosoma*-associated disease to be treated can be any infectious disease caused by *Trypanosoma* parasites, and can be, for example, trypanosomiasis, or more specifically, African trypanosomiasis or American trypanosomiasis.

Note that a symptom specific to the *Trypanosoma*-associated disease is not particularly limited. Examples of the symptom include, in a case of African trypanosomiasis, symptoms which appear in respective two phases after an asymptomatic phase. Examples of a symptom appearing in the first phase include fever, lymphadenopathy, hepatosplenomegaly, systemically histiomonocytic disseminated lesion by *Trypanosoma* parasites, and the like. Examples of a symptom appearing in the second phase include sensory disorders (e.g., convulsions, radiculalgia, neuralgia, hyperesthesia, and the like), mental disorders (e.g., simple personality change and the like), sleep disorders (e.g., sleeplessness at night and the like), movement disorders (e.g., paralysis caused by pseudotumors, convulsive seizure, shivering, abnormal chorea or athetoid movement, impaired synkinesis due to cerebellar dysergia, extrapyramidal reduced reflex action, and the like), and neurological and endocrine disorders (e.g., disorder of thermoregulation, dry mouth, loss of sexual desire, amenorrhea, infertility, pituitary hyperthyroidism, and the like).

Further, in the case of American trypanosomiasis, examples of a symptom appearing in an acute phase include fever, splenomegaly, and the like. In a case where American trypanosomiasis develops into a chronic form, examples of a symptom include chronic cardiac disorders (e.g., angina-like precordial pain, arrhythmia, conduction disturbance, left heat failure or right and left heart failure, embolism, and the like), organomegaly (e.g., megaesophagus or the like), chronic encephalopathy, and the like. Note that the symptoms described above appear solely or in combination.

Treatment in the present invention denotes causing an activity of *Trypanosoma* parasites in a human or an animal to be suppressed as compared with a case where no measure is taken for the human or the animal. The treatment preferably denotes prevention of infection by *Trypanosoma* parasites, more preferably, killing of *Trypanosoma* parasites. Note here that the prevention of infection means inhibiting an infection-related activity of *Trypanosoma* parasites so that the *Trypanosoma* parasites cannot infect the human or the animal. An aspect of the treatment includes (i) reduction or alleviation of at least one symptom associated with the *Trypanosoma*-associated disease and (ii) reduction or alleviation of a combination of one or more symptoms related to the *Trypanosoma*-associated disease.

(Human or Animal to which Therapeutic Agent is Administered)

A subject of the treatment is a human or animal which is a host to *Trypanosoma* parasites. More specifically, the subject of the treatment is any one selected from a group consisting of mammals on which *Trypanosoma* parasites can be parasitic, including humans. Among the group consisting of mammals, a therapeutic method according to the present invention is particularly suitably applicable to mammals. The type of a mammal to be treated is not particularly limited, and can be experimental animals such as mice, rats, rabbits, guinea pigs, and primates other than humans; pet animals (pets) such as dogs and cats; farm animals such as pigs, cattle, goats, sheep, and horses; and humans, preferably farm animals or humans, and particularly preferably humans.

(Types of *Trypanosoma* Parasites and *Trypanosoma*-Associated Disease Caused by Each Type)

A type of *Trypanosoma* parasites which are a subject of the treatment and the infection prevention, or the killing is not particularly limited, as long as it is *Trypanosoma* parasites that can be parasitic on the human or animal. It is known that various *Trypanosoma*-associated diseases are caused depending on a type of *Trypanosoma* parasites.

*Trypanosoma* parasites that cause American trypanosomiasis (Chagas disease) are, for example, *Trypanosoma cruzi* (*T. cruzi*). *Trypanosoma* parasites that cause human African trypanosomiasis (African sleeping sickness), which is a type of African trypanosomiasis developed in humans, are, for example, *Trypanosoma brucei* complexes. A *Trypanosoma brucei* complex includes *T. brucei rhodensiense* and/or *T. brucei gambiense*. Nagana, which is an example of animal African trypanosomiasis developed in animals other than humans, is caused in a case where animals including farm animals become infected by *T. brucei brucei, T. congolense, T. vivax*, or the like. Further, sura, which is another example of animal African trypanosomiasis, is caused in a case where animals including farm animals become infected by *T. evansi* or the like.

(Morphologies of *Trypanosoma* Parasites which are Subject of Treatment and Infection Prevention, or Killing)

A form of *Trypanosoma* parasites which are the subject of the treatment and the prevention of infection, or the killing may be any form of a life cycle.

For example, *Trypanosoma cruzi* has four different forms. Trypomastigote is an infection phase form appearing in mammalian blood. After invading mammalian cells, trypomastigotes transform into spherical amastigotes (intracellular growth phase form), and start growth. Amastigotes grow in any type of mammalian cells, particularly significantly in cells of striated muscles such as a myocardium or of a lymphonodus. The amastigotes eventually transform into trypomastigotes, destroy infected cells, and are released into a blood flow as a bloodstream form of trypomastigote. The *Trypanosoma* parasites taken into a vector insect reduviid when the reduviid sucks blood of the mammalian host transform into epimastigotes and undergo repeated division in an alimentary canal of the reduviid. Further, the epimastigotes transform into metacyclic trypomastigotes in the alimentary canal of the reduviid. Then, the metacyclic trypomastigotes are released out of the body of the reduviid together with feces of the reduviid, and invade the body of a mammalian host through a wound or a mucosa. In this way, an infection cycle is repeated. *Trypanosoma cruzi* in any of these forms can be the subject of the treatment and the prevention of infection, or the killing.

Other types of *Trypanosoma* parasites, in any of the trypomastigote, amastigote, epimastigote, and metacyclic trypomastigote forms, can also be the subject of the treatment and the prevention of infection, or the killing. In order to maximize effects of the treatment and the prevention of infection, or the killing, it may be preferable that *Trypanosoma* parasites in the form trypomastigote, which is an infection phase form, or in the form of amastigote, which is an intracellular growth phase form, be the subject of the treatment and the infection prevention, or the killing. Further, among the forms of trypomastigote, it may be more preferable that *Trypanosoma* parasites in a bloodstream form of trypomastigote be the subject of the treatment and the infection prevention, or the killing.

(Infection Routes of *Trypanosoma* Parasites which are Subject of Treatment and Infection Prevention, or Killing)

A route through which a human or an animal is infected by *Trypanosoma* parasites is not particularly limited.

It is known that the route of infection differs depending on a type of *Trypanosoma* parasites which causes each *Trypanosoma*-associated disease.

For example, *T. brucei gambiense* and *T. brucei rhodensiense*, each of which causes African trypanosomiasis, and *Trypanosoma* parasites, which cause nagana that is a type of African trypanosomiasis, cause infection through intermediation of a tsetse fly, which is a fly belonging to the genus *Glossina* of the family Muscidae. Infection intermediated by a tsetse fly occurs when *Trypanosoma* parasites are injected into the body of a human or an animal through the salivary gland of the tsetse fly while the tsetse fly sucks the blood from the human or the animal. Further, *T. evansi* is intermediated by hematophagia by a gadfly and a stable fly.

Further, *Trypanosoma cruzi*, which is a pathogen of Chagas disease, causes infection through intermediation of a reduviid, which is an insect belonging to the family Reduviidae of the order Hemiptera. At the same time as the reduviid sucks the blood from a human or an animal, the reduviid drops, onto the skin of the human or the animal, feces (in a liquid form) which contain a large quantity of *Trypanosoma cruzi* in a trypomastigote form. The infection is caused when the feces are rubbed into the body through a wound, a mucosa, or the like.

Further, examples of an infection route of *Trypanosoma* parasites other than the above include transfusion of blood (infected blood) containing *Trypanosoma* parasites, organ transplantation from an infected person, mother-to-child transmission via a placenta, mother-to-child transmission by breast-feeding of the infected mother's milk, infection via an injection needle, infection by intake of food (raw juice, raw meat, or the like) contaminated with *Trypanosoma* parasites in an infectious form, and the like.

($IP_3R$ Protein of *Trypanosoma* Parasites)

A therapeutic agent of the present invention for treating a *Trypanosoma*-associated disease contains, as a medicinal component, an antisense oligonucleotide which suppresses the expression of an $IP_3R$ protein of *Trypanosoma* parasites. Note that 'suppresses the expression of an $IP_3R$ protein of *Trypanosoma* parasites' means, for example, suppression of the transcription and/or translation of mRNA encoding an $IP_3R$ protein of *Trypanosoma* parasites.

Also note here that 'an $IP_3R$ protein of *Trypanosoma* parasites' means a transmembrane protein which is a $Ca^{2+}$ channel of *Trypanosoma* parasites and has a function of causing $Ca^{2+}$ signaling by being activated when binding to $IP_3$. The $IP_3R$ protein of *Trypanosoma* parasites is distributed, for example, locally at the ER, and causes $IP_3$-mediated $Ca^{2+}$ release ($Ca^{2+}$ ion transport to the outside of the ER) at ER to thereby initiate $Ca^{2+}$ signaling.

Specific examples of the $IP_3R$ protein of *Trypanosoma* parasites can be as follows.

1) Protein having the amino acid sequence of SEQ ID NO: 9.

2) Protein having 80% or more sequence identity with the amino acid sequence of SEQ ID NO: 9 and having a function of causing $IP_3$-mediated $Ca^{2+}$ transport by binding with $IP_3$. Note that the sequence identity with the amino acid sequence of SEQ ID NO: 9 is preferably 85% or more, more preferably 90% or more, 95% or more, 96% or more, 97% or more, or 98% or more, and particularly preferably 99% or more.

3) Protein (i) having an amino acid sequence in which 1 to 602 amino acids are substituted, deleted, inserted, and/or added in the amino acid sequence of SEQ ID NO: 9 and (ii) having a function of causing $IP_3$-mediated $Ca^{2+}$ transport. Note that the number of amino acids substituted, deleted, inserted, and/or added is preferably 1 to 451, more preferably 1 to 301, further more preferably 1 to 150, and particularly preferably 1 to 120, 1 to 90, 1 to 60, 1 to 30, 1 to 6, or 1 to 5.

4) Protein (i) having 70% or more sequence identity with (a) an amino acid sequence which is included in the amino acid sequence of SEQ ID NO: 9 and located in a transmembrane domain (2533rd to 2786th amino acids) and (b) an amino acid sequence in a gatekeeper domain (2787th to 3011th amino acids), which domains are conserved in $IP_3R$ between different species and (ii) having a function of causing $IP_3$-mediated $Ca^{2+}$ transport by binding with $IP_3$. Note that the sequence identity with the amino acid sequences (a) and (b) is preferably 80% or more, more preferably 90% or more, 95% or more, 96% or more, 97% or more, or 98% or more, and particularly preferably 99% or more.

Note that the amino acid sequence of SEQ ID NO: 9 is an amino acid sequence of an $IP_3R$ ($TcIP_3R$) protein derived from *Trypanosoma cruzi*, which amino acid sequence was isolated by the inventors of the present invention. As for *Trypanosoma* parasites other than *Trypanosoma cruzi*, the amino acid sequence of SEQ ID NO: 11 is known as an amino acid sequence of an $IP_3R$ ($TbIP_3R$) protein derived from *T. brucei brucei* (Reference: Huan G, et al., Proc Natl Acad Sci USA 110:1887-92, 2013).

(Antisense Oligonucleotide)

In the present invention, the antisense oligonucleotide against a gene encoding an $IP_3R$ protein of *Trypanosoma* parasites is used as a medicinal component to suppress the expression of the $IP_3R$ protein. That is, a therapeutic agent of the present invention for treating a *Trypanosoma*-associated disease uses an antisense method in which the expression of a target protein is suppressed by use of a single-stranded oligonucleotide that is hybridizable with mRNA (sense strand) encoding the target protein.

Note that the meaning of 'the antisense oligonucleotide is hybridizable with mRNA (sense strand) encoding a protein' is not limited to a case where a base sequence of the antisense oligonucleotide and a base sequence of mRNA are completely complementary with each other in a domain where hybridization can occur. For example, in a case where the domain in which hybridization can occur has a length not shorter than 20 bp, the antisense oligonucleotide may be an oligonucleotide having 80% or more, more preferably 85% or more, further more preferably 90% or more, particularly preferably 95% or more sequence identity with a sequence that is completely complementary with a base sequence of mRNA in the domain. Or alternatively, the antisense oligonucleotide may be an oligonucleotide which is different from the completely complementary sequence by five or less base sequences, preferably four or less base sequences, more preferably three or less base sequences, further more preferably two or less base sequences, particularly preferably one base sequence.

In a therapeutic agent according to one embodiment for treating a *Trypanosoma*-associated disease, the antisense oligonucleotide includes a base sequence which is hybridizable with at least a part of mRNA of $IP_3R$ of the *Trypanosoma* parasites.

Examples of such an antisense oligonucleotide include an oligonucleotide including the base sequence of SEQ ID NO: 1, an oligonucleotide including the base sequence of SEQ ID NO: 2, an oligonucleotide including the base sequence of SEQ ID NO: 3, and an oligonucleotide including the base sequence of SEQ ID NO: 4. The base sequences of SEQ ID NO: 1 to SEQ ID NO: 4 are sequences which are complementary with the 1778th to 1797th base sequence, the 5532nd to 5551st base sequence, the 5996th to 6015th base sequence, and the 8647th to 8666th base sequence, respectively, in the base sequence of SEQ ID NO: 10 of DNA in a coding region of TcIP$_3$R (mRNA of TcIP$_3$R in the coding region represented by substituting a uracil base with a thymine base also has the same sequence).

A preferable aspect of the antisense oligonucleotide is an oligonucleotide consisting of the base sequence of SEQ ID NO: 1, an oligonucleotide consisting of the base sequence of SEQ ID NO: 2, an oligonucleotide consisting of the base sequence of SEQ ID NO: 3, and an oligonucleotide consisting of the base sequence of SEQ ID NO: 4. Another preferable aspect of the antisense oligonucleotide is an oligonucleotide consisting of a base sequence having 80% or more sequence identity with any one of the base sequences of SEQ ID NO: 1 to SEQ ID NO: 4. Note that the sequence identity with the any one of the base sequences of SEQ ID NO: 1 to SEQ ID NO: 4 is preferably 80% or more, more preferably 85% or more, and further more preferably 90% or more or 95% or more.

Note that a plurality of types of antisense oligonucleotides may be contained in a single therapeutic agent for treating a Trypanosoma-associated disease.

The antisense oligonucleotide may be designed, for example, on the basis of a base sequence of genomic DNA, cDNA or mRNA of IP$_3$R of Trypanosoma parasites. For example, in a case where Trypanosoma parasites are Trypanosoma cruzi, an antisense oligonucleotide may be designed on the basis of the base sequence of SEQ ID NO: 10 which is a base sequence of mRNA in a coding region of TcIP$_3$R and represented by substituting a base sequence and a uracil base of DNA in the coding region with a thymine base. Information of the base sequence of genomic DNA, cDNA or mRNA of IP$_3$R of Trypanosoma parasites is available, for example, from GenBank and the like. For example, the base sequence of genomic DNA and the base sequence of mRNA of TcIP$_3$R have GenBank accession number AB701320. Further, the base sequence of DNA in the coding region of TbIP$_3$R and the base sequence of mRNA in the coding region represented by substituting a uracil base with a thymine base have NCBI reference number XM_842017 (SEQ ID NO: 12).

The antisense oligonucleotide may be any of a DNA molecule, an RNA molecule, and a hybrid molecule of DNA and RNA. From the viewpoint of stability, a DNA molecule may be preferable.

Further, the antisense oligonucleotide may be a native nucleotide or a normative nucleotide. Examples of the normative nucleotide include a phosphorothioate type, 2'-O, 4'-C-ethylene bridged nucleic acids (ENA), a peptide nucleic acid (PNA), and the like. These normative nucleotides are not easily degraded by nuclease and, accordingly, act in cells efficiently. In particular, the 2'-O,4'-C-ethylene bridged nucleic acid (ENA) or the like having a higher nuclease resistance may be preferable.

The antisense oligonucleotide can be obtained by a publicly known genetic engineering technique and a nucleotide synthesis method. Specifically, the antisense oligonucleotide can be prepared by use of a known method such as chemical synthesis, in vitro translation, or the like.

Further, in a therapeutic agent of the present invention for treating a Trypanosoma-associated disease, the antisense oligonucleotide may be provided, for example, (i) in a form which is contained as it is in the therapeutic agent so as to be administered as it is to a human or an animal or (ii) in a form which is incorporated in a downstream of an appropriate promoter sequence so as to be administered to a human or an animal as an antisense RNA expression vector.

A vector in which a nucleotide encoding the antisense oligonucleotide is incorporated is not particularly limited, but examples of the vector encompass (i) a virus vector such as an adenovirus vector, an adeno-associated virus vector, a herpesvirus vector, a vaccinia virus vector, and a retrovirus vector and (ii) a vector applicable to gene therapy, such as a plasmid vector. The virus vector is preferably altered so as to lack self-replicating ability.

It is preferable that an expression regulatory sequence which causes the antisense oligonucleotide to be expressed specifically to Trypanosoma parasites be incorporated in the vector. Note here that the expression regulatory sequence is, for example, a promoter or an enhancer, and more specifically, a promoter sequence of ribosomal RNA derived from Trypanosoma parasites, or the like.

Construction of an expression vector can be performed by use of a publicly known genetic engineering technique.

Note that 'causes a nucleotide to be expressed specifically to Trypanosoma parasites' refers to a state in which the nucleotide is substantially not expressed in a human or an animal to be treated and is expressed only in Trypanosoma parasites. This enables an effect of a gene therapy agent to work selectively on Trypanosoma parasites.

(Other Components and Dosage Form of Therapeutic Agent for Treating Trypanosoma-Associated Disease)

A therapeutic agent of the present invention for treating a Trypanosoma-associated disease may further include components other than the antisense oligonucleotide described above. The components other than the antisense oligonucleotide are not particularly limited, but can be, for example, a pharmaceutically acceptable carrier, a lubricant, a preservative, a stabilizer, a wetting agent, an emulsifier, salts for osmotic adjustment, a buffer, a colorant, a flavoring agent, a sweetener, an antioxidant, a viscosity modifier, and the like. Further, if necessary, a therapeutic agent for treating a Trypanosoma-associated disease such as suramin, pentamidine, eflornithine, melarsoprol, benznidazole, nifurtimox, or the like can be added as an element constituting a therapeutic agent of the present invention for treating a Trypanosoma-associated disease so as to constitute a complex drug.

The pharmaceutically acceptable carrier is not particularly limited, but it is preferable that the pharmaceutically acceptable carrier be a carrier and have a characteristic that, in a case where the carrier is administered together with the therapeutic agent for treating a Trypanosoma-associated disease, the carrier neither inhibits the function (treatment of a Trypanosoma-associated disease) of the therapeutic agent nor give a substantive negative influence on the human or the animal to which the therapeutic agent is administered.

A wide range of carriers already reported in the technical field can be employed as the carrier. Specifically, examples of the carrier include, but not particularly limited to, water, various salt solutions, alcohol, vegetable oil, polyethylene glycol, gelatin, lactose, amylose, magnesium stearate, talc, silicic acid, paraffin, fatty acid monoglyceride, fatty acid diglyceride, hydroxymethylcellulose, polyvinyl pyrrolidone, and the like. A type of the carrier may be selected as appropriate in accordance with a dosage form, an administration route, and the like of the therapeutic agent for treating a Trypanosoma-associated disease.

The dosage form of the therapeutic agent for treating a Trypanosoma-associated disease is not particularly limited as well. Examples of the dosage form encompass tablets, pills, powder, solutions, suspensions, emulsions, granules, capsules, suppositories, injections, and the like, preferably injections or a dosage form for oral administration. For example, a dosage form for oral administration such as tablets is preferable from the viewpoint of portability, easy administration and the like, and injections are preferable from the viewpoint of controlling a concentration of the therapeutic agent in blood to be within a predetermined range at predetermined timing. Further, the therapeutic agent for treating a *Trypanosoma*-associated disease can be a liposomal preparation.

[2. Method for Treating *Trypanosoma*-Associated Disease]

(Administration Method and Dosage)

A therapeutic method of the present invention of treating a *Trypanosoma*-associated disease includes a step of administering, to a human or an animal, a therapeutically effective amount of at least one of the above-described therapeutic agents for treating a *Trypanosoma*-associated disease. In one embodiment, the human or the animal to which the at least one of the above-described therapeutic agents is administered is infected by *Trypanosoma* parasites. Note here that the therapeutic agent for treating a *Trypanosoma*-associated disease may be administered alone, or administered as a component of a pharmacological composition suitable for an objective of the administration.

A method of administrating the therapeutic agent for treating a *Trypanosoma*-associated disease is not particularly limited. The therapeutic agent may be administered systemically by means of a technique such as oral administration, intravascular administration into a vein or an artery, or enteral administration, or locally by means of a technique such as transdermal administration, sublingual administration, or the like. In one preferred administration mode, in order to exert an action on *Trypanosoma* parasites living in a blood circulatory system (in blood), the therapeutic agent is administered systemically by intravenous administration or intraarterial administration. In another preferred administration mode, the therapeutic agent is administered by oral administration, since the oral administration is advantageous in terms of ease of administration and the like.

A dosage (therapeutically effective amount) of the therapeutic agent for treating a *Trypanosoma*-associated disease can be set as appropriate in accordance with the age, sex, and body weight of the human or the animal to which the therapeutic agent is administered, the symptom, the administration route, the number of doses, the dosing period, and the like. Further, if necessary, an in vivo assay using the therapeutic agent for treating a *Trypanosoma*-associated disease can be carried out in advance so as to determine the dosage without the need of excessive experiments.

The number of doses of the therapeutic agent for treating a *Trypanosoma*-associated disease is also not particularly limited, as long as a therapeutic effect is obtained. For example, the number of doses can be set as appropriate in accordance with the type of therapeutic agent for treating a *Trypanosoma*-associated disease, the dosage, the administration route, the symptom, the age, sex, and weight of the human or animal, and the like.

An administration timing of the therapeutic agent for treating a *Trypanosoma*-associated disease is also not particularly limited as long as a therapeutic effect is obtained. In order to maximize the therapeutic effect, it may be preferable that the administration timing be determined in accordance with the form of *Trypanosoma* parasites in the human or the animal. For example, it may be more preferable that the administration timing of the therapeutic agent be determined so that the concentration of the therapeutic agent in blood will be a therapeutically effective amount during a period in which *Trypanosoma* parasites in the human or the animal is in the form of trypomastigote.

Note that the scope of the therapeutic method of the present invention also includes a dosage form which is like what is called preventive administration and in which the therapeutic agent for treating a *Trypanosoma*-associated disease is administered to a human or an animal at timing before infection by *Trypanosoma* parasites. That is, in this dosage mode, a state in which a concentration of the therapeutic agent in blood is maintained at or above a therapeutically effective amount is created before the human or the animal is infected by *Trypanosoma* parasites, and a therapeutic effect is obtained when the human or the animal becomes infected by the *Trypanosoma* parasites.

Note that the form of *Trypanosoma* parasites in the human or the animal can easily be understood by a person skilled in the art. Examples of a method of understanding the form include preparing a thick blood film and dying the thick blood film by a technique such as Giemsa stain, and then conducting a microscopic observation of *Trypanosoma* parasites. In a case where *Trypanosoma* parasites grow with periodicity, it is possible, once a form of the *Trypanosoma* parasites is checked, to predict which form the *Trypanosoma* parasites will take after a certain period of time.

Further, by carrying out an in vivo assay or the like if necessary, a person skilled in the art can easily understand a concentration of the therapeutic agent in the blood of the human or the animal, more specifically, a relationship between a dosage, administration timing, and concentration in blood of the therapeutic agent.

(Combination Therapy)

In the therapeutic method of the present invention of treating a *Trypanosoma*-associated disease, the therapeutic agent of the present invention for treating a *Trypanosoma*-associated disease may be combined with another therapeutic agent, other than the therapeutic agent of the present invention, for treating a *Trypanosoma*-associated disease, the another therapeutic agent being suramin, pentamidine, eflornithine, melarsoprol, benznidazole, nifurtimox, or the like (combination therapy). The therapeutic method of the present invention of treating a *Trypanosoma*-associated disease is a new therapeutic method which uses a mechanism different from that of a conventional therapeutic agent for treating a *Trypanosoma*-associated disease. Therefore, it is expected that employment of the combination therapy enables to provide a synergistic therapeutic effect between a conventional therapeutic method and dramatically improve treatment results.

[3. Drug]

A drug of the present invention is a drug for suppressing the expression of an $IP_3R$ protein of *Trypanosoma* parasites, the drug containing, as an active component, an antisense oligonucleotide which suppresses the expression of the $IP_3R$ protein.

The antisense oligonucleotide contained in the drug of the present invention can be understood by referring to corresponding descriptions in the section [1. Therapeutic Agent for Treating *Trypanosoma*-associated Disease].

In the drug of the present invention, the antisense oligonucleotide can be provided, for example, (i) in a form which is contained as it is in the drug so as to be administered as it is to a subject or (ii) in a form which is incorporated in a downstream of an appropriate promoter sequence so as to be administered to a subject as an antisense RNA expression vector. The vector in which a nucleotide encoding the antisense oligonucleotide is incorporated can be understood by referring to corresponding descriptions in the section [1. Therapeutic Agent for Treating *Trypanosoma*-associated Disease].

Further, the drug of the present invention may further include components other than the antisense oligonucleotide. The components other than the antisense oligonucleotide can be understood by referring to corresponding descriptions in the section [1. Therapeutic Agent for Treating *Trypanosoma*-associated Disease].

[4. Method for Preventing Infection by *Trypanosoma* Parasites, or Killing *Trypanosoma* Parasites]

A method of the present invention of killing *Trypanosoma* parasites is a method which includes a step of supplying an 'effective amount' of the drug to *Trypanosoma* parasites.

Note here that the 'effective amount' means an amount which enables to prevent infection by *Trypanosoma* parasites, more preferably, an amount which enables to kill *Trypanosoma* parasites. The effective amount is set by a person skilled in the art as appropriate in accordance with conditions such as a habitat environment of *Trypanosoma* parasites to which the drug is administered.

In a case where *Trypanosoma* parasites which is a subject of the infection prevention or the killing is present in a place other than a living organism (for example, in an incubation medium for *Trypanosoma* parasites, cultured cells of a biological sample such as blood, or the like), the drug can be added to the incubation medium for *Trypanosoma* parasites, the biological sample, a cell culture solution, or the like. Further, in a case where the drug is applied to *Trypanosoma* parasites in cells, the antisense oligonucleotide can be introduced into the cells by means of lipofection, microinjection, and the like.

The biological sample and the cultured cells are, for example, derived from a human or an animal which is a host of *Trypanosoma* parasites. More specifically, it is preferable that the biological sample and the cultured cells be derived from any one(s) selected from the group consisting of mammals including humans. A type of mammals is not particularly limited, but can be, for example, experimental animals such as mice, rats, rabbits, guinea pigs, and primates other than humans; pet animals (pets) such as dogs and cats; farm animals such as cattle, pigs, goats, sheep, and horses; and humans, preferably farm animals and humans, and particularly preferably humans.

Examples of application of the method of preventing infection by *Trypanosoma* parasites, or killing *Trypanosoma* parasites include supplying the drug to blood having or at risk of infection by *Trypanosoma* parasites, thereby suppressing a risk of secondary infection with Trypanosomes. For example, the concept of the blood is not particularly limited but encompasses blood collected through blood donation activities, blood for blood transfusion, blood shed during outdoor activities (including traffic accidents etc.), blood shed in a medical setting, and blood extracted out of the body of a human or an animal.

Note that examples of a method of checking an effect of killing *Trypanosoma* parasites include preparing a thick blood film, then dying the thick blood film by means of a technique such as Giemsa stain, and then conducting a microscopic observation of *Trypanosoma* parasites.

Apart from the above, a type, form, and the like of *Trypanosoma* parasites to which the method is applied can be understood by referring to corresponding descriptions in the section [1. Therapeutic Agent for Treating *Trypanosoma*-associated Disease].

[5. Method of Screening Candidate for Therapeutic Agent for Treating *Trypanosoma*-Associated Disease]

A screening method according to the present invention for screening a candidate for a therapeutic agent for treating a *Trypanosoma*-associated disease includes (i) a first step of adding, in vitro and while *Trypanosoma* parasites are in a trypomastigote form, a drug to be screened and then (ii) a second step of selecting the drug as a candidate for the therapeutic agent in a case where the addition of the drug has caused growth of the *Trypanosoma* parasites to be suppressed, caused infection of the *Trypanosoma* parasites to be prevented, or caused the *Trypanosoma* parasites to be killed.

The screening method of the present invention is a method which is based on the knowledge that, in a case where an agent capable of suppressing an expression level of an $IP_3R$ protein of *Trypanosoma* parasites is administered when *Trypanosoma* parasites are in a trypomastigote form, growth of the *Trypanosoma* parasites is suppressed, infection by the *Trypanosoma* parasites, is prevented, or the *Trypanosoma* parasites are killed. The screening method of the present invention allows screening of a candidate for a therapeutic agent whose action mechanism is different from that of a conventional therapeutic agent.

In the first step, how to perform synchronized culture and how to check a form of the *Trypanosoma* parasites are not particularly limited.

The screening method of the present invention can also be interpreted as a screening method for screening a candidate for an agent for preventing infection by the *Trypanosoma* parasites, or killing *Trypanosoma* parasites.

EXAMPLES

The following description will discuss the present invention more specifically on the basis of Examples and Reference Examples below, but the present invention is not limited to these.

Chemotherapy of the Chagas disease currently depends mainly on two types of therapeutic agents benznidazole and nifurtimox, both of which have a harmful side effect. Therefore, it is important to develop a new drug for treating the Chagas disease. Examples of new means for treating an infectious disease include the antisense oligonucleotide. The use of the antisense oligonucleotide is aimed at knocking down a causal essential component in a pathogen.

[Material and Method]

The following description will first discuss a material and a method which are common between the Examples and the Reference Examples.

(1) Culture of *T. cruzi* and Host Cells

Epimastigotes of *T. cruzi*, Tulahuen strain were cultured in a medium in accordance with an already reported method (Reference: Iizumi K, et al., Biochim Biophys Acta 1758: 738-746, 2006). Subsequently, in accordance with an already reported method (Reference: Gluenz E, et al., Int J Parasitol 37:617-625, 2007), trypomastigotes were induced. In accordance with an already reported method (Reference: Nakajima-Shimada J, et al., Antimicrob Agents Chemother 40:2455-2458, 1996), the trypomastigotes were caused to infect 3T3-SWISS Albino cells (Health Science Research Bank), an in vitro incubation system and an in vitro infection system were established and maintained, and trypomastigotes which appeared in the culture were collected by centrifugal separation. For experimental infection in vitro, 3T3-SWISS Albino cells and human-derived HeLa cells were used.

(2) Plasmid for Over-expression of Recombinant TcIP$_3$R

For preparation of *T. cruzi* which over-expresses recombinant TcIP$_3$R (EGFP-TcIP$_3$R) to which an enhanced green fluorescent protein (EGFP) was fused, a plasmid prepared in accordance with an already reported method (Reference: Hashimoto M, et al., Mol Microbiol 87:1133-1150, 2013) was used.

(3) Antibody and Reagent

An anti-TcIP$_3$R monoclonal antibody was prepared in accordance with an already reported method (Reference: Hashimoto M, et al., Mol Microbiol 87:1133-1150, 2013). An anti-EGFP antibody (Molecular Probes, Inc., Eugene, Oreg.) and an anti-tubulin antibody (Thermo Fisher Scientific, Inc., Rockford, Ill.) were purchased. Cycloheximide (Wako Pure Chemical Industries, Ltd.) was purchased. Quick-CBB PLUS (Wako Pure Chemical Industries, Ltd.) was used for CBB staining. Western blotting was carried out in accordance with an existing report (Reference: Murata E, et al., Microbiol Immunol 52:539-543, 2008).

(4) Oligonucleotide

A phosphorothioate-type oligonucleotide was designed, and was purchased from Integrated DNA Technologies, Inc. (Diego, Calif.). The sequences of SEQ ID NOs: 1, 2, 3 and 4 are sequences which are respectively complementary with sequences of SEQ ID NOs: 5, 6, 7, and 8, which are sense sequences of a TcIP$_3$R gene.

Reference Example 1: Determination of Property of TcIP$_3$R Protein

The antisense oligonucleotide inhibits expression of a protein by inhibiting transcription of mRNA or translation of polypeptide or destabilizing mRNA, or peptide synthesis. As such, a short-lived protein is a desirable subject of an effective and functional knockdown by the antisense oligonucleotide. In order to check whether or not the TcIP$_3$R is suitable for a strategy of the antisense oligonucleotide, epimastigotes of *T. cruzi* were cultured in the presence of Cycloheximide (CHX), which is a protein synthesis inhibiting agent, and degradation of the TcIP$_3$R protein was observed over time by western blotting.

Results are shown in A of FIG. 1. FIG. 1 is a view showing a life span of the TcIP$_3$R protein in epimastigotes of *T. cruzi*. A of FIG. 1 is a view showing an expression level of a native TcIP$_3$R protein in epimastigotes. B of FIG. 1 is a view showing an expression level of a recombinant EGFP-TcIP$_3$R fusion protein. Epimastigotes of *T. cruzi* were cultured in the presence of 200 μg/mL of CHX for each time period shown in FIG. 1, and were analyzed by western blotting with use of an anti-TcIP$_3$R antibody. An expression level of the TcIP$_3$R protein was normalized to an expression level of tubulin to show a relative ratio (%).

As shown in A of FIG. 1, an expression level of the TcIP$_3$R protein rapidly declined after a CHX treatment. It is possible to conclude from this result that the TcIP$_3$R protein is a short-lived protein, and in order to examine an accurate half-life, the following experiment was conducted.

In the same way as the experience shown in A of FIG. 1, epimastigotes which over-express EGFP-TcIP$_3$R were cultured in the presence of CHX, and western blotting was carried out with use of an anti-TcIP$_3$R antibody. As a control, epimastigotes which express EGFP alone were subjected to the experiment.

Figure 3:
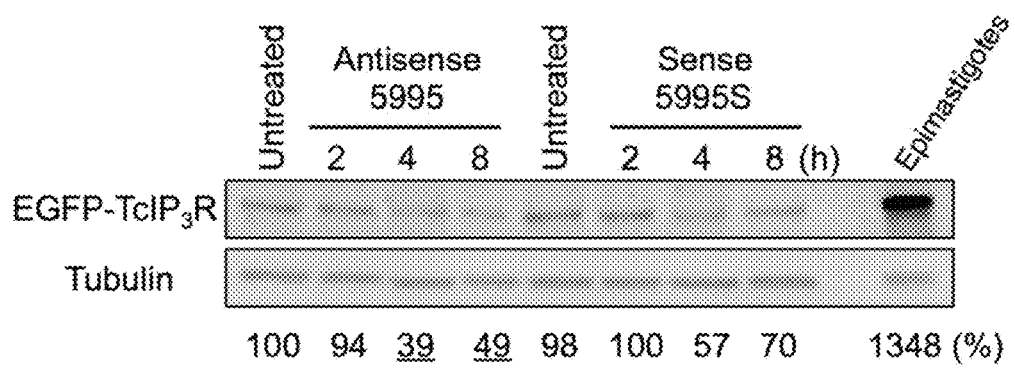
FIG. 3 is a view showing an antisense oligonucleotide against TcIP$_3$R suppresses TcIP$_3$R protein expression in trypomastigotes.

Results are shown in B of FIG. 1. B of FIG. 1 is a view showing an expression level of a recombinant EGFP-TcIP$_3$R fusion protein. As shown in B of FIG. 1, an expression level of EGFP in the control barely changed, whereas an expression level of EGFP-TcIP$_3$R declined over time. This shows that degradation specific to TcIP$_3$R and probably proteasome-dependent was occurring. Further, a half-life of EGFP-TcIP$_3$R was approximately three hours. In contrast, it is known that a half-life of the IP$_3$R protein in an unstimulated cultured cell of a mammal is 10 to 12 hours (Reference: Wojcikiewicz R J H, WIRES Membr Transp Signal 1:126-135, 2012). This shows that the TcIP$_3$R protein is less stable than the IP$_3$R protein of a mammal. It was therefore concluded that the TcIP$_3$R protein is a short-lived protein. The antisense oligonucleotide can effectively exert an action on the short-lived TcIP$_3$R protein. Accordingly, the short-lived TcIP$_3$R protein is an effective target of a therapeutic agent for treating Chagas disease.

Reference Example 2: $TcIP_3R$ Protein Level in Trypomastigotes

The inventors of the present invention showed that transcription of mRNA of $TcIP_3R$ constantly occurs through a life cycle of *T. cruzi*, and a transcriptional level differs depending on a form of the *T. cruzi* and is the lowest in trypomastigotes. In the present Reference Example, western blotting using an anti-$TcIP_3R$ monoclonal antibody was carried out to examine how an expression level of the $TcIP_3R$ protein differs depending on a developmental stage. As an internal control, western blotting was carried out with use of an antitubulin antibody. Results are shown in FIG. 2. As shown in FIG. 2, the $TcIP_3R$ protein is detected in epimastigotes (E) but not detected in trypomastigotes (T). The results suggest that a level of the $TcIP_3R$ protein in trypomastigotes is very low. This result shows that the antisense oligonucleotide exerts an action more effectively in a case where the antisense oligonucleotide targets the trypomastigote form, which is the only infectious form of *T. cruzi*. The result accordingly shows that the antisense oligonucleotide can exert an action effectively as a therapeutic agent for treating Chagas disease.

The low level of the $TcIP_3R$ protein in trypomastigotes is advantageous as a target of a treatment using the antisense oligonucleotide for the following reasons. Firstly, since trypomastigote is the only infectious form of *T. cruzi*, the treatment can effectively inhibit infection. Secondly, since trypomastigotes do not undergo division, a concentration of the antisense oligonucleotide taken into a cell can be stable. Thirdly, since the antisense oligonucleotide is taken into trypomastigotes without requiring a special treatment (Reference: Malaga S, Yoshida N. Infect Immun 69:353-359, 2001), $IP_3R$ protein expression can be suppressed efficiently. Further, it is assumed that, since nucleotide and amino acid sequences of $TcIP_3R$ has very little homology with that of $IP_3R$ of mammals including humans, side effects are not easily produced. $TcIP_3R$ is thus suitable for use as a target of the treatment which uses the antisense oligonucleotide.

Example 1: Suppression of $TcIP_3R$ Protein Expression Using $TcIP_3R$-Specific Antisense Oligonucleotide Evaluation was made as to whether or not a treatment using a $TcIP_3R$-specific antisense oligonucleotide can actually prevent $TcIP_3R$ protein expression in trypomastigotes. Since no $TcIP_3R$ protein was detected in a trypomastigotes (see B of FIG. 1), trypomastigotes which over-express EGFP-$TcIP_3R$ were cultured in the presence of an antisense oligonucleotide (SEQ ID NO: 3: Antisense 5995) or a sense oligonucleotide (SEQ ID NO: 7: Sense 5995S), and western blotting was carried out with use of an anti-EGFP antibody. As an expression control of EGFP-TcIP$_3$R, untreated epimastigotes which over-express EGFP-TcIP$_3$R were used. As an internal control, western blotting was carried out with use of an antitubulin antibody. Results are shown in FIG. 3.

Also in *T. cruzi* which over-express EGFP-TcIP$_3$R, a significant decline was observed in EGFP-TcIP$_3$R protein expression level in trypomastigotes. This shows that a TcIP$_3$R-specific degradation activity is extremely strong in trypomastigotes. In a case where the treatment using the antisense oligonucleotide of SEQ ID NO: 3 was carried out, an EGFP-TcIP$_3$R expression level declined to 40% in four hours after the co-culture. These results show that TcIP$_3$R expression in trypomastigotes can be suppressed efficiently by means of an antisense oligonucleotide treatment. Further, a decline in EGFP-TcIP$_3$R expression level was observed also in the treatment using the sense oligonucleotide of SEQ ID NO: 7. This revealed that the sense nucleotide was causing suppression of expression on a transcriptional level.

The experimental results above show that the TcIP$_3$R-specific antisense oligonucleotide is effective for use as a component of a therapeutic agent for treating Chagas disease.

Example 2: Prevention of Trypomastigote Infection Using TcIP$_3$R-Specific Antisense Oligonucleotide Whether or not the TcIP$_3$R-specific antisense oligonucleotide suppresses cell invasion of trypomastigotes was considered. Trypomastigotes were cultured for eight hours in the presence of 40 μM of a phosphorothioate-type oligonucleotide, and the trypomastigotes were caused to infect 3T3-SWISS Albino cells with a ratio of trypomastigote:host cell=10:1 (multiplicity of infection, MOI). Twelve hours later, the number of amastigotes per two hundred (200) host cells was counted. The data shown are each the mean±standard deviation of three independent experiments. For assessment of a significant difference between experimental groups, ANOVA and Fischer's PLSD post hoc test were used. Results are shown in A of FIG. 4.

Figure 4:
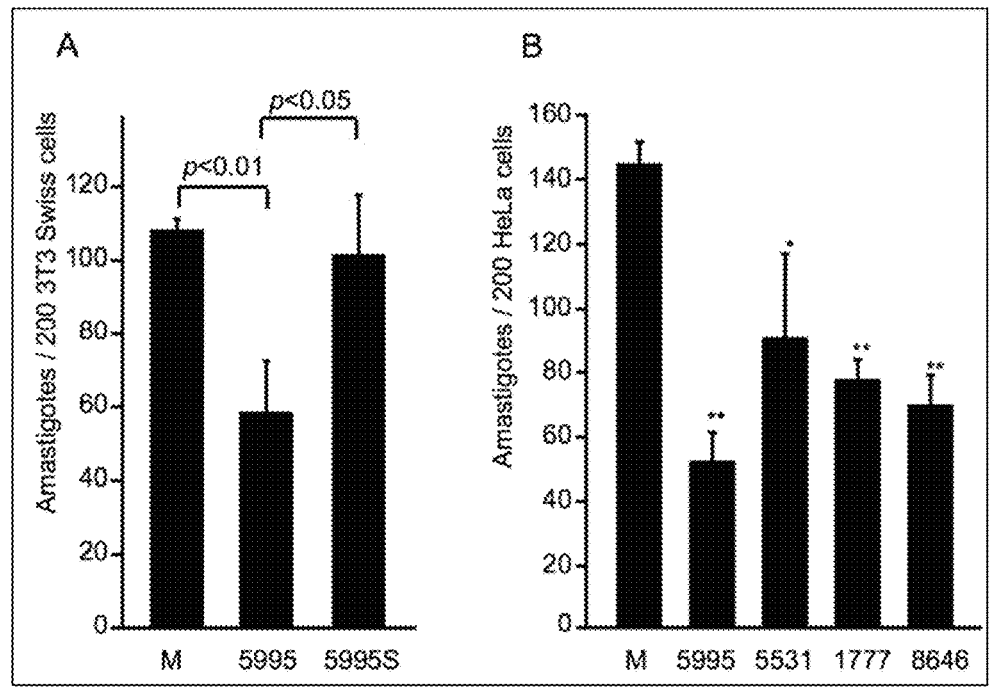
FIG. 4 is a view showing an inhibitory effect of a TcIP$_3$R-specific antisense oligonucleotide exhibited against cell invasion by trypomastigotes. A of FIG. 4 shows the number of amastigotes per 200 3T3-SWISS albino cells (10 MOI) obtained in a case where trypomastigotes ($2\times10^5$) were treated with 40 µM of a phosphorothioated antisense oligonucleotide (SEQ ID NO: 3) or a phosphorothioated sense oligonucleotide (SEQ ID NO: 7) for eight hours, and were incubated at 37° C. for 12 hours together with $4\times10^4$ mouse fibroblasts (3T3-SWISS albino). B of FIG. 4 shows the number of amastigotes per two hundred (200) HeLa cells (10 MOI) obtained in a case where trypomastigotes ($4\times10^5$) were treated for eight hours with use of 40 µM of phosphorothioated oligonucleotide (SEQ ID NOs: 1, 2, 3, and 4) and incubated at 37° C. for 12 hours together with $4\times10^4$ HeLa cells.

FIG. 4 is a view showing an inhibitory effect of the TcIP$_3$R-specific antisense oligonucleotide exhibited against cell invasion by trypomastigotes. A of FIG. 4 shows the number of amastigotes per two hundred (200) 3T3-SWISS albino cells (10 MOI) obtained in a case where trypomastigotes ($2\times10^5$) were treated with 40 μM of a phosphorothioated antisense oligonucleotide (SEQ ID NO: 3) or a phosphorothioated sense oligonucleotide (SEQ ID NO: 7) for eight hours, and were incubated at 37° C. for 12 hours together with $4\times10^4$ mouse fibroblasts (3T3-SWISS albino).

As shown in A of FIG. 4, in a case where the trypomastigotes were treated with the antisense oligonucleotide of SEQ ID NO: 3, the number of infected amastigotes significantly decreased compared to a case where the trypomastigotes were untreated (M) and a case where the trypomastigotes were treated with the sense oligonucleotide of SEQ ID NO: 7. These results match results obtained by using single TcIP$_3$R gene-knockout *T. cruzi*, and show that suppression of TcIP$_3$R protein expression lowers an infectious ability of trypomastigotes.

In order to examine whether or not the antisense oligonucleotide has specificity in targeting a DNA sequence, three types of TcIP$_3$R-specific antisense oligonucleotides set to respective different domains (SEQ ID NOs: 1, 2, and 4) were used, in addition to the antisense oligonucleotide of SEQ ID NO: 3, to examine an effect of preventing trypomastigote infection. An experiment similar to the experiment shown in A of FIG. 4 was conducted, in which human-derived HeLa cells were used as host cells. Results are shown in B of FIG. 4.

B of FIG. 4 shows the number of amastigotes per two hundred (200) HeLa cells (10 MOI) obtained in a case where trypomastigotes ($4\times10^5$) were treated for eight hours with use of 40 μM of phosphorothioated oligonucleotide (SEQ ID NOs: 1, 2, 3, and 4) and incubated at 37° C. for 12 hours together with $4\times10^4$ HeLa cells.

All of the antisense oligonucleotides thus used in the experiment induced a decrease in infectious ability of trypomastigotes. The results show that the antisense oligonucleotide has a low selectivity as to where to target in a sequence, and can be designed to target basically any region in a coding region for the TcIP$_3$R gene or mRNA of TcIP$_3$R in the sequence.

Therefore, it is shown that an antisense oligonucleotide targeting TcIP$_3$R is effective for use as a component of a therapeutic agent for treating Chagas disease.

The present invention is not limited to the above-described embodiments but allows various modifications within the scope of the claims. In other words, any embodiment derived from a combination of two or more technical means appropriately modified within the scope of the claims will also be included in the technical scope of the present invention. All references cited in this specification are incorporated herein by reference in their entireties.

INDUSTRIAL APPLICABILITY

The present invention is applicable, for example, to treatment and research of a *Trypanosoma*-associated disease, development of a therapeutic agent for treating a *Trypanosoma*-associated disease, and the like.

The invention claimed is:

1. A therapeutic agent for treating a *Trypanosoma*-associated disease, comprising, as a medicinal component, a therapeutically effective amount of a synthesized antisense oligonucleotide suppressing the expression of an inositol 1,4,5-trisphosphate receptor protein of *Trypanosoma* parasites,
   wherein the therapeutic agent further comprises at least a preservative.

2. The therapeutic agent as set forth in claim 1, wherein:
   the synthesized antisense oligonucleotide is at least two selected from the group consisting of an oligonucleotide including the base sequence of SEQ ID NO: 1, an oligonucleotide including the base sequence of SEQ ID NO: 2, an oligonucleotide including the base sequence of SEQ ID NO: 3, an oligonucleotide including the base sequence of SEQ ID NO: 4, an oligonucleotide including a base sequence having 90% or more sequence identity with the base sequences of SEQ ID NO: 1, an oligonucleotide including a base sequence having 90% or more sequence identity with the base sequences of SEQ ID NO: 2, an oligonucleotide including a base sequence having 90% or more sequence identity with the base sequences of SEQ ID NO: 3, and an oligonucleotide including a base sequence having 90% or more sequence identity with the base sequences of SEQ ID NO: 4.

3. The therapeutic agent as set forth in claim 1, wherein:
   the synthesized antisense oligonucleotide is at least two selected from the group consisting of an oligonucleotide consisting of the base sequence of SEQ ID NO: 1, an oligonucleotide consisting of the base sequence of SEQ ID NO: 2, an oligonucleotide consisting of the base sequence of SEQ ID NO: 3, an oligonucleotide consisting of the base sequence of SEQ ID NO: 4, an oligonucleotide consisting of a base sequence having 90% or more sequence identity with the base sequences of SEQ ID NO: 1, an oligonucleotide consisting of a base sequence having 90% or more sequence identity with the base sequences of SEQ ID NO: 2, an oligonucleotide consisting of a base sequence having 90% or more sequence identity with the base sequences of SEQ ID NO: 3, and an oligonucleotide consisting of a base sequence having 90% or more sequence identity with the base sequences of SEQ ID NO: 4.

4. A drug for suppressing the expression of an inositol 1,4,5-trisphosphate receptor protein of *Trypanosoma* parasites, comprising, as an active component, an effective amount of a synthesized antisense oligonucleotide suppressing the expression of the inositol 1,4,5-trisphosphate receptor protein,
   wherein the drug further comprises at least a preservative.

* * * * *